United States Patent [19]

Leslie et al.

[11] Patent Number: 4,529,401
[45] Date of Patent: Jul. 16, 1985

[54] AMBULATORY INFUSION PUMP HAVING PROGRAMMABLE PARAMETERS

[75] Inventors: James E. Leslie, Moundsview; Everett D. Anderson, Maplewood, both of Minn.

[73] Assignee: Cardiac Pacemakers, Inc., St. Paul, Minn.

[21] Appl. No.: 338,327

[22] Filed: Jan. 11, 1982

[51] Int. Cl.³ ............................................. A61M 5/00
[52] U.S. Cl. .................................. 604/131; 604/67; 604/155; 128/DIG. 1; 128/DIG. 12
[58] Field of Search ....................... 604/19, 27, 30, 31, 604/65, 66, 67, 131, 155; 128/DIG. 12, DIG. 13, DIG. 1

[56] References Cited

U.S. PATENT DOCUMENTS

| | | | |
|---|---|---|---|
| 3,701,345 | 10/1972 | Heilman et al. | 128/DIG. 1 X |
| 4,077,405 | 3/1978 | Haerten et al. | 128/DIG. 12 X |
| 4,137,913 | 2/1979 | Georgi | 604/67 |
| 4,146,029 | 3/1979 | Ellinwood | 128/419 P |
| 4,149,419 | 4/1979 | Connell, Jr. et al. | 128/660 |
| 4,245,634 | 1/1981 | Albisser et al. | 604/66 |
| 4,270,532 | 6/1981 | Fronetzki et al. | 604/65 |
| 4,308,866 | 1/1982 | Jelliffe et al. | 604/67 X |
| 4,373,527 | 2/1983 | Fischell | 128/DIG. 12 X |
| 4,469,481 | 9/1984 | Kobayashi | 604/131 X |

OTHER PUBLICATIONS

Martin, P. et al., "Normalization of Insulin Delivery to Diabetics by Pulsed Insulin Infusion", IEEE BME Trans., vol. 24, No. 2, Mar. 1977, pp. 116–121.

A. M. Albisser, "Devices for the Control of Diabetes Mellitus", IEEE, vol. 67, No. 9, Sep. 1979, pp. 1308–1320.

Primary Examiner—Kyle L. Howell
Assistant Examiner—Francis J. Jaworski
Attorney, Agent, or Firm—Orrin M. Haugen; Thomas J. Nikolai; Douglas L. Tschida

[57] ABSTRACT

A portable infusion pump for controllably supplying a programmed volume of medicant to a patient. The apparatus generally comprises a small, portable container having a keyboard for programming the mode of operation and operating parameters, whereby a microprocessor controls the pump in the various BASAL, SUPPLEMENTAL OR MANUAL dose delivery modes. The apparatus also contains a photo-coupler controlled driven lead screw assembly for controlling the stroke of the syringe plunger, whereby metered doses of the medicant are injected into the patient; display means for confirming programmed inputs; means for audibly warning of error conditions; and means for recording the total cummulative dosage delivered.

22 Claims, 75 Drawing Figures

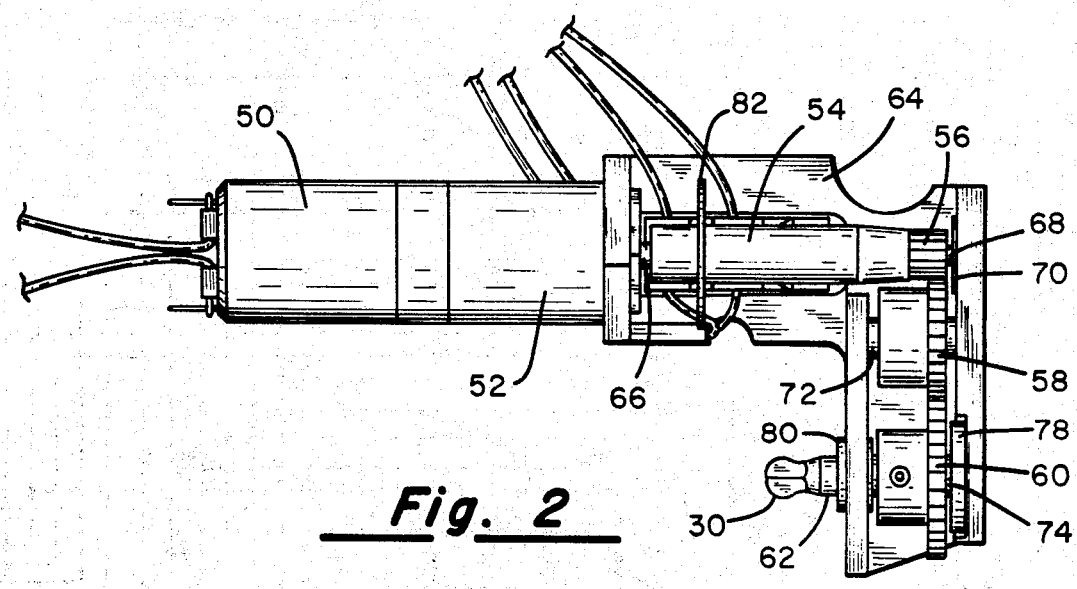
Fig. 2
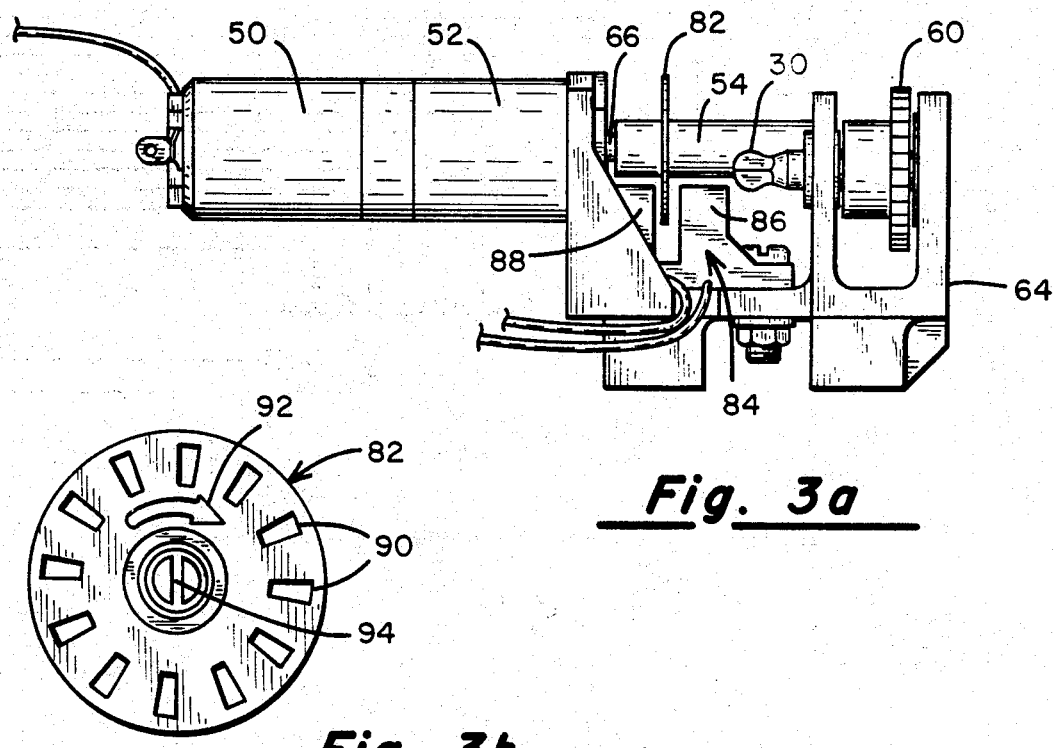
Fig. 3a
Fig. 3b

DO

NAME

QUESTION

SUBROUTINE CALL

SUBROUTINE RETURN

TAG

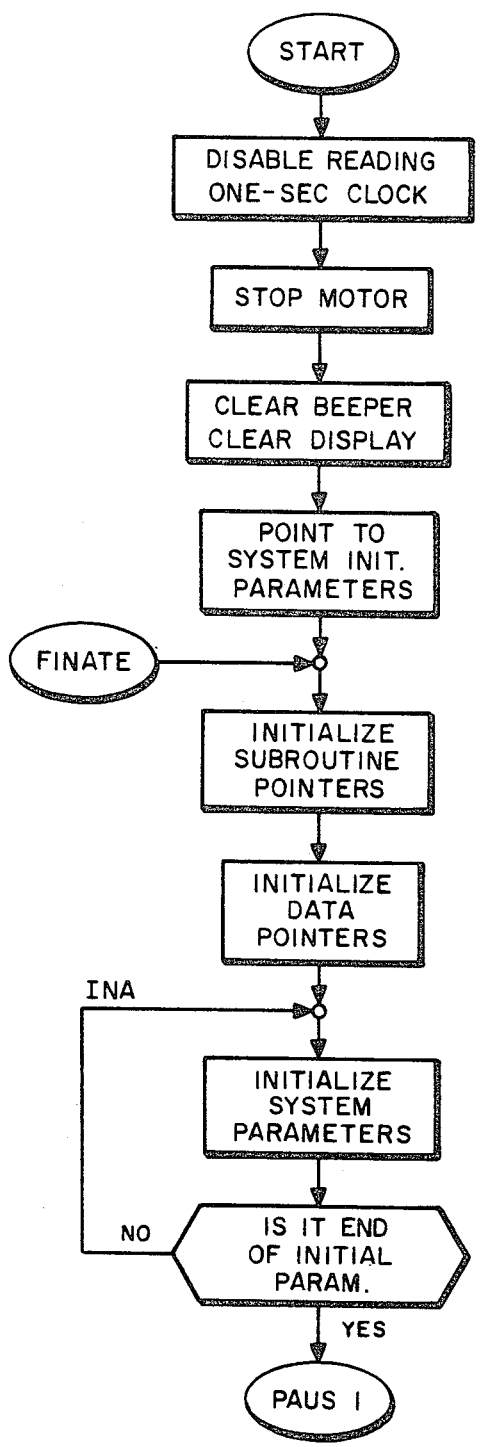
Fig. 5.1
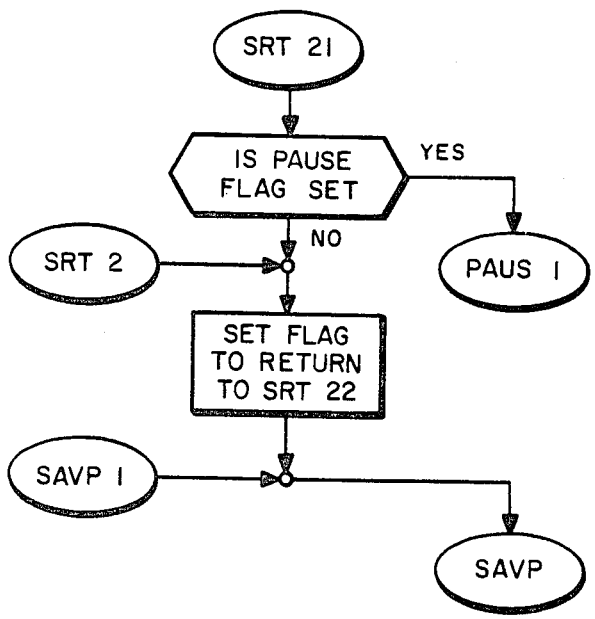
Fig. 5.2

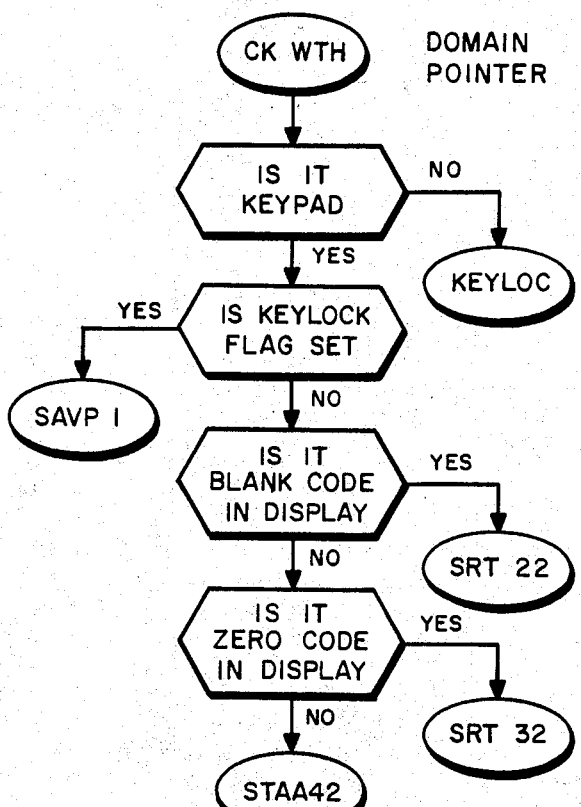
Fig. 5.3
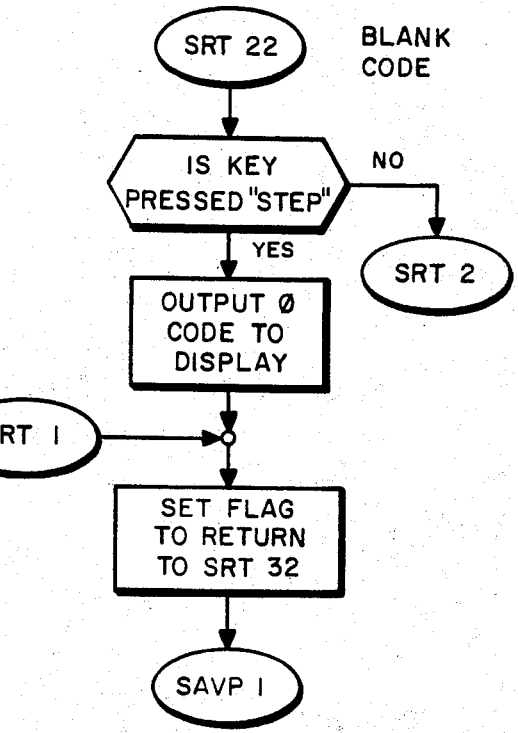
Fig. 5.4

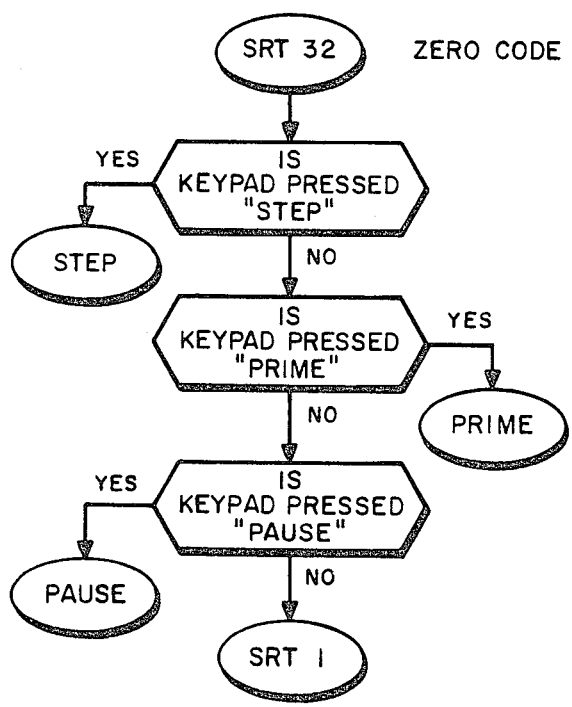
Fig. 5.5
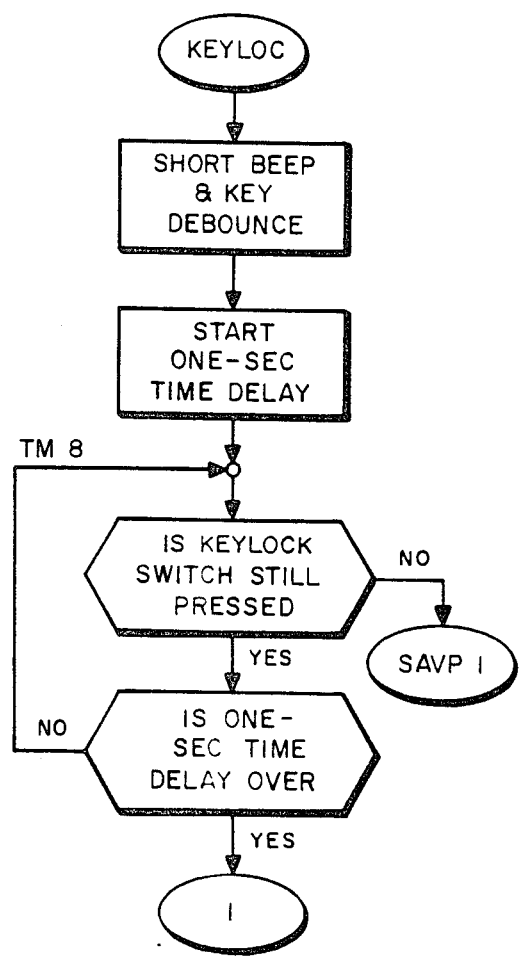
Fig. 5.6

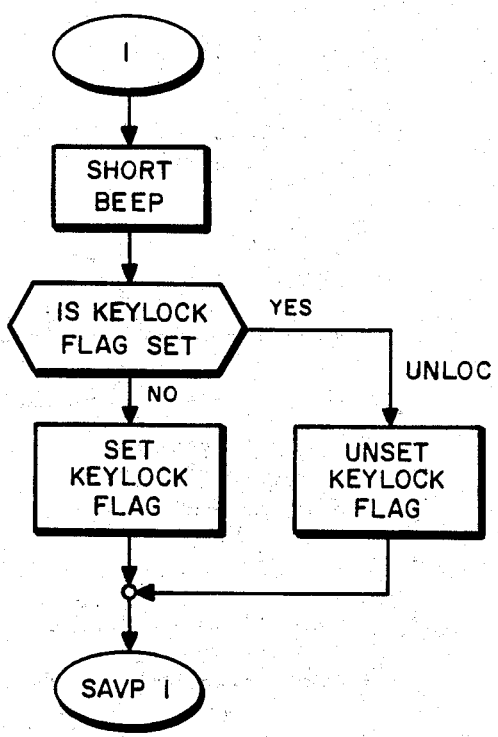
Fig. 5.7
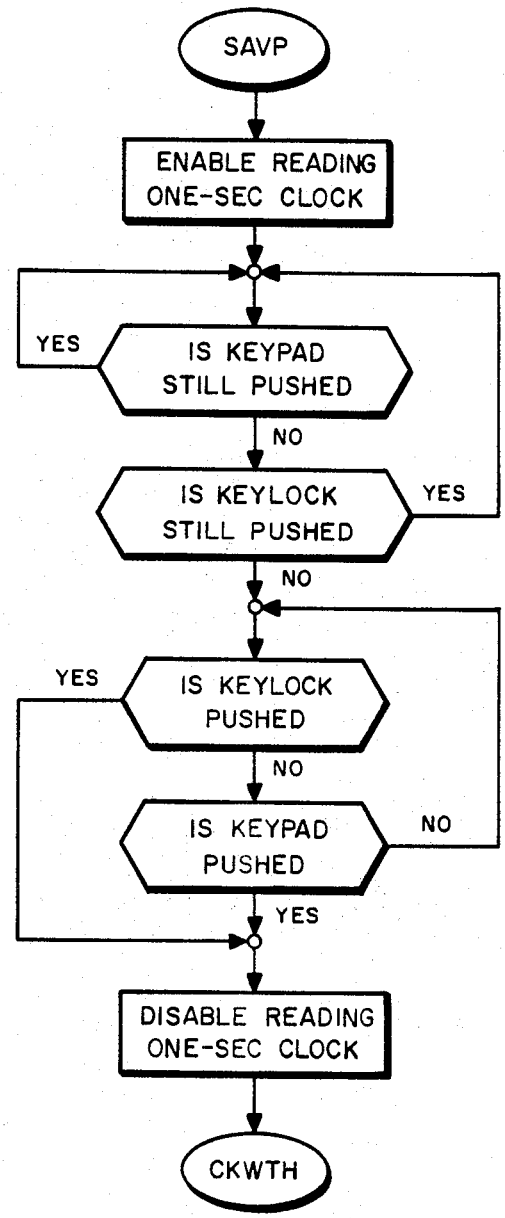
Fig. 5.8

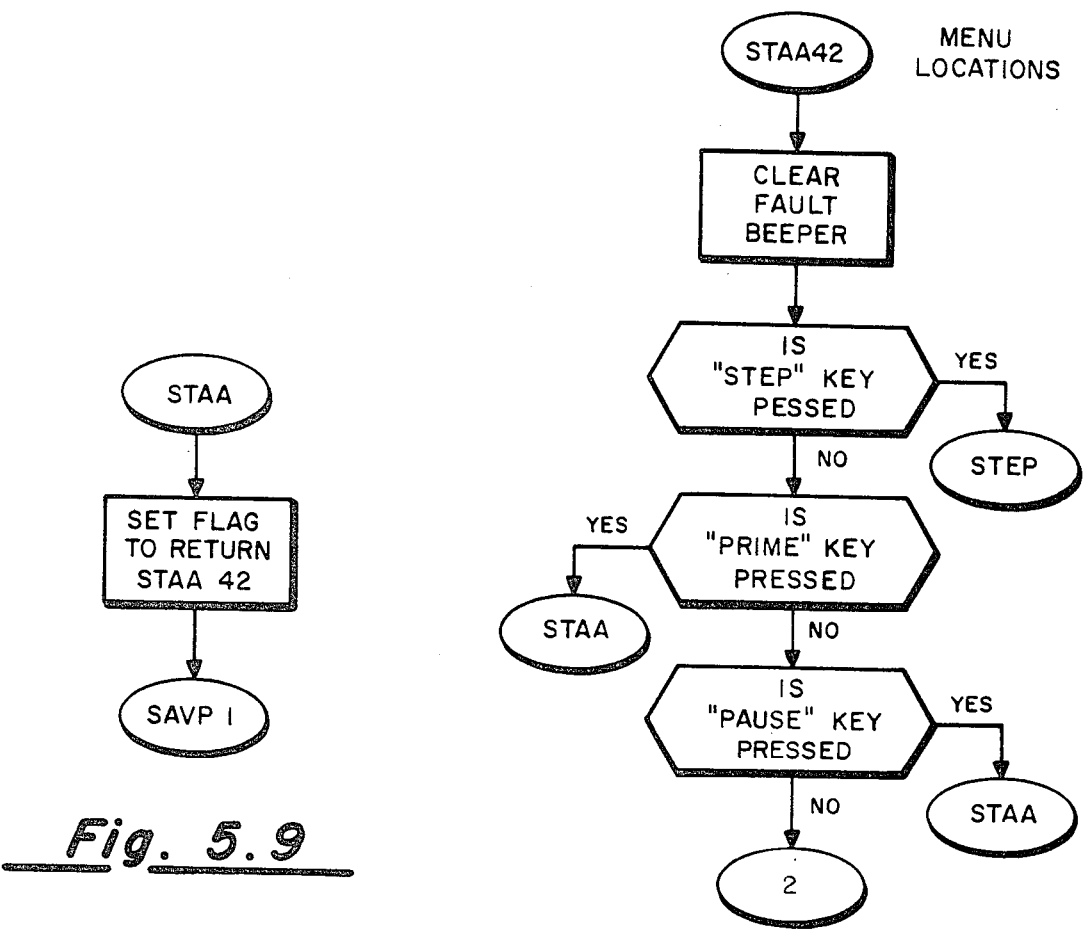
Fig. 5.9
Fig. 5.10

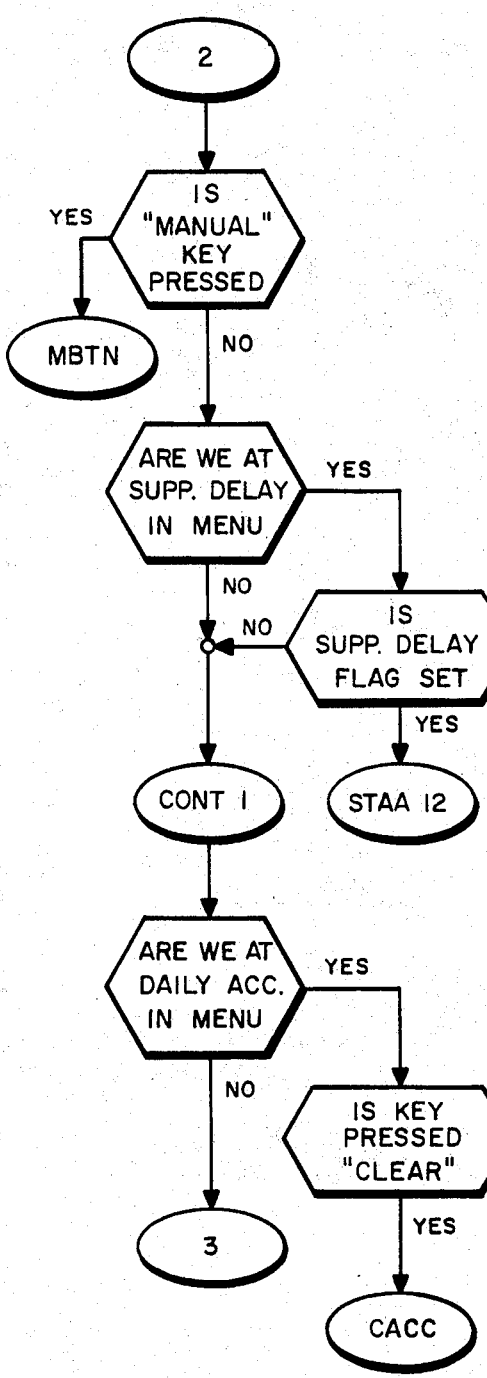
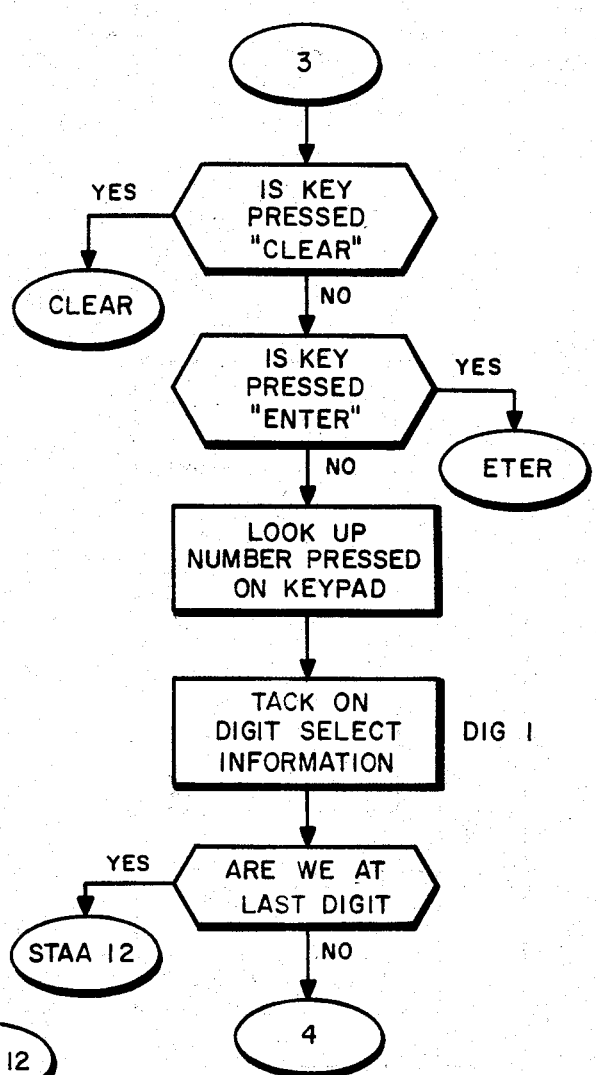
Fig. 5.11
Fig. 5.12

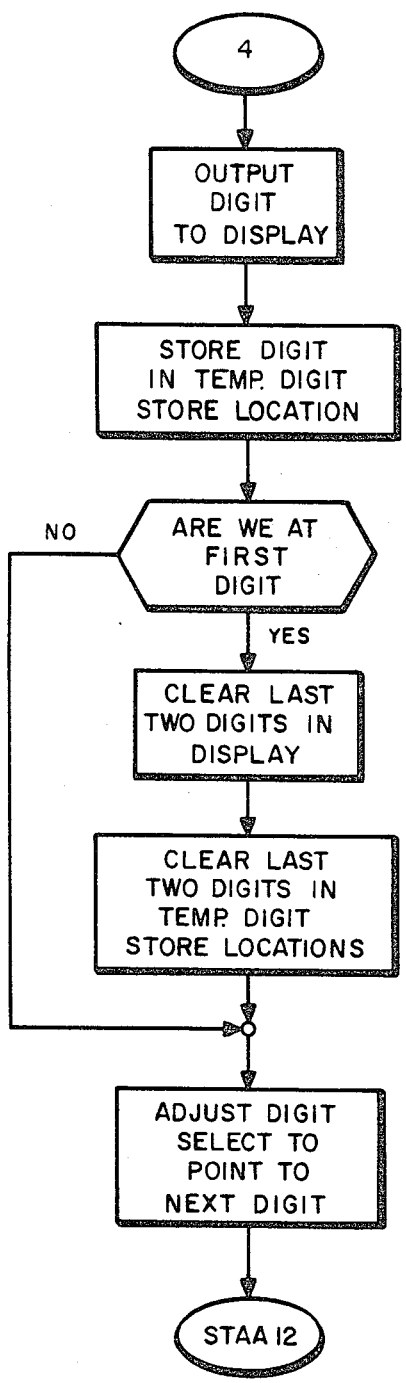
Fig. 5.13
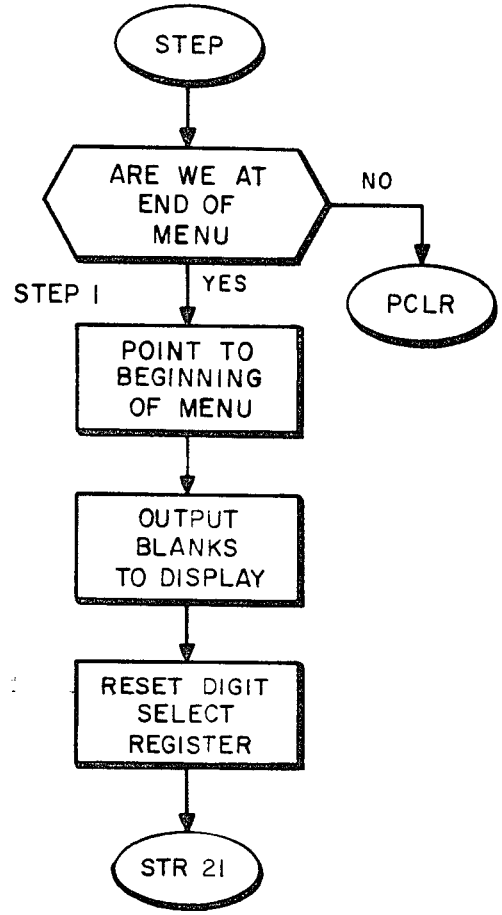
Fig. 5.14

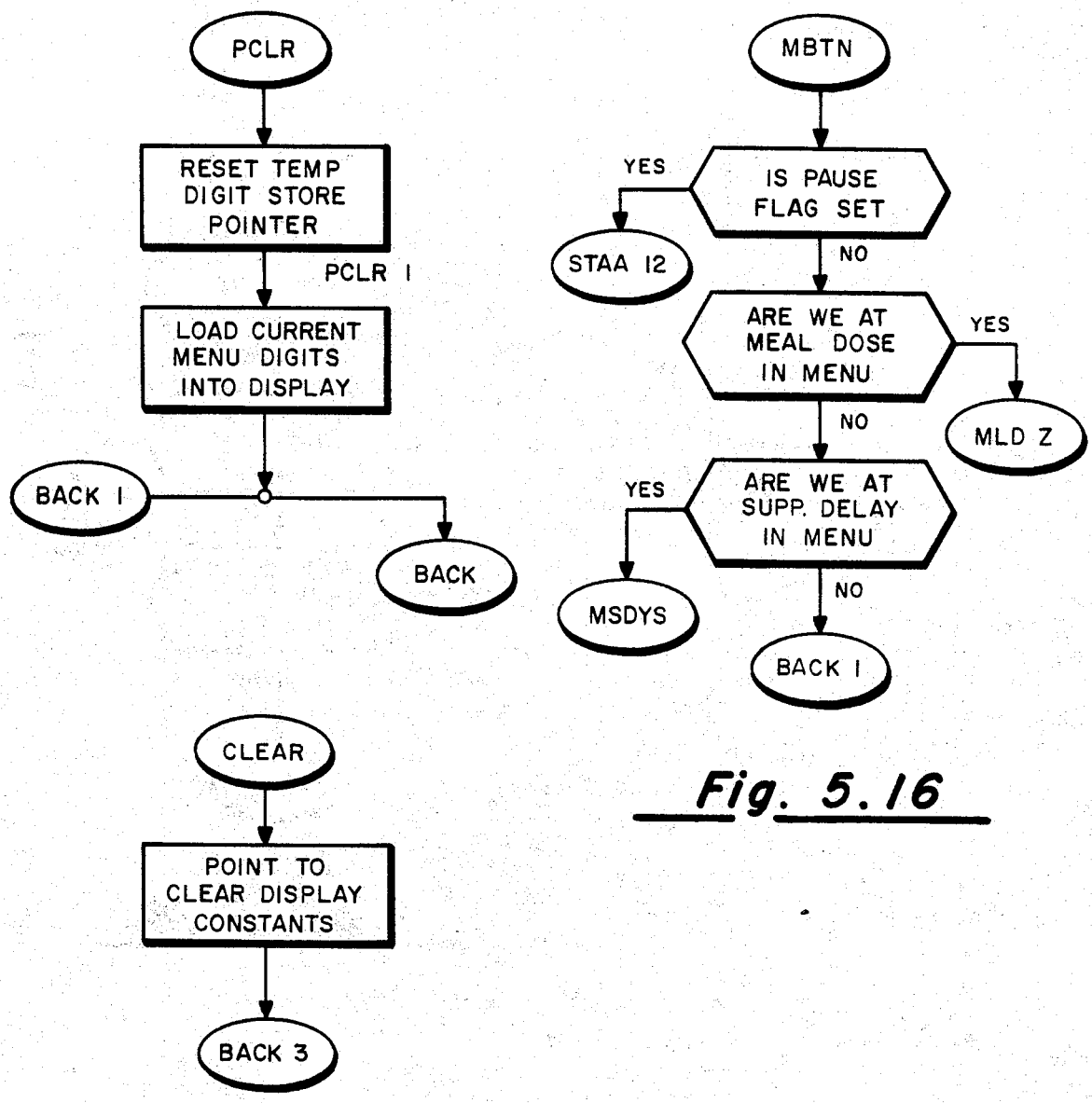
Fig. 5.15
Fig. 5.16

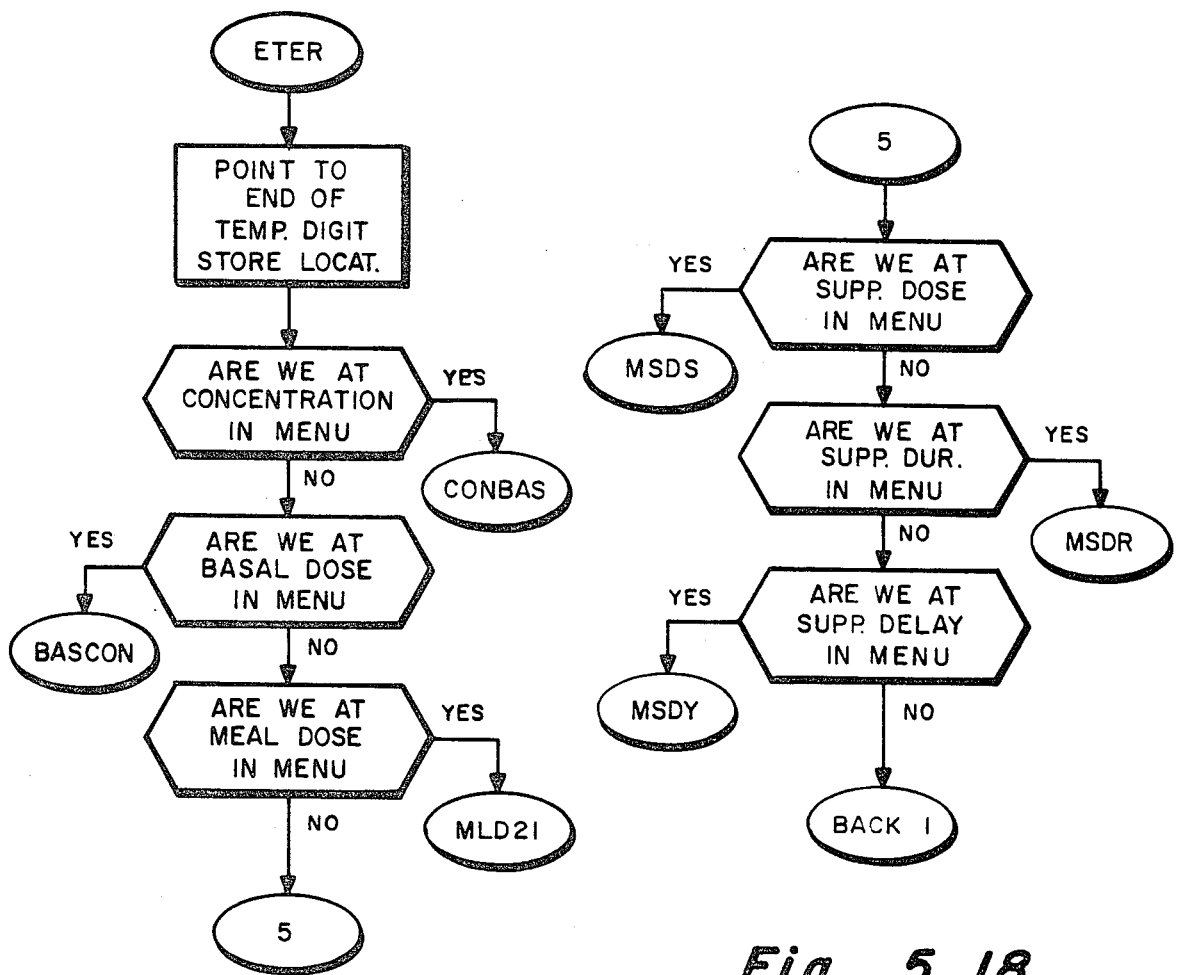
Fig. 5.17
Fig. 5.18

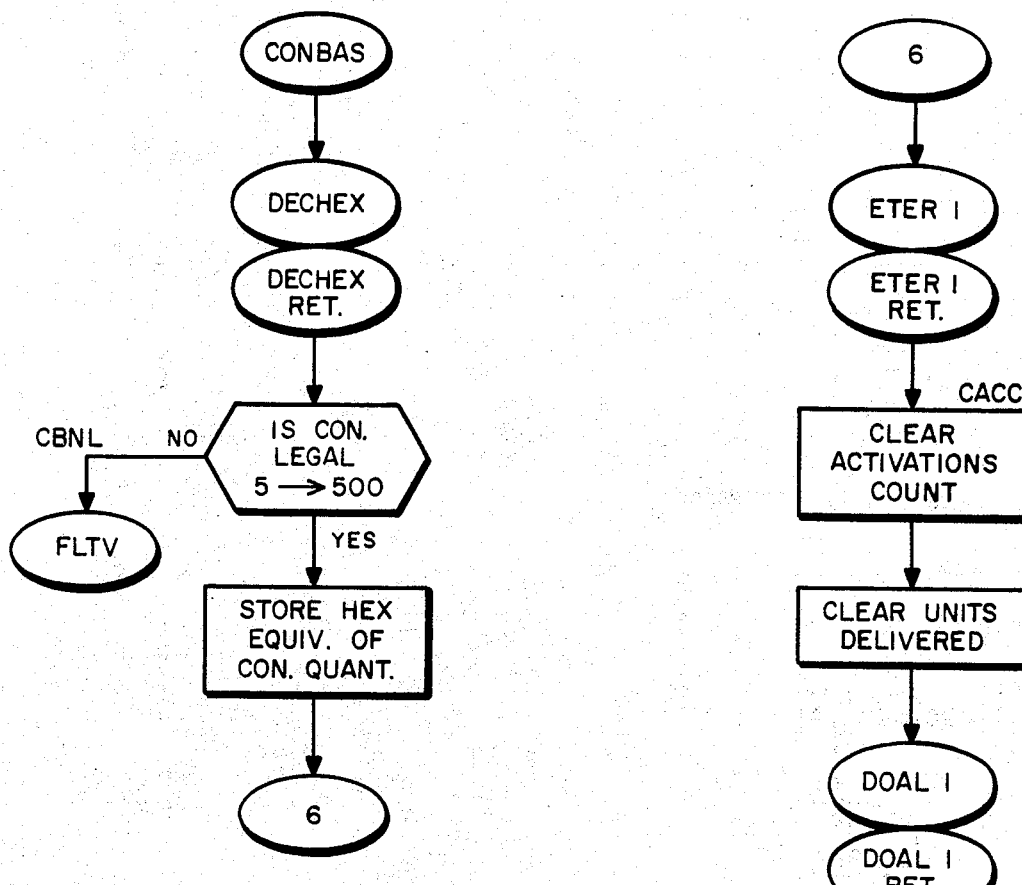
Fig. 5.19
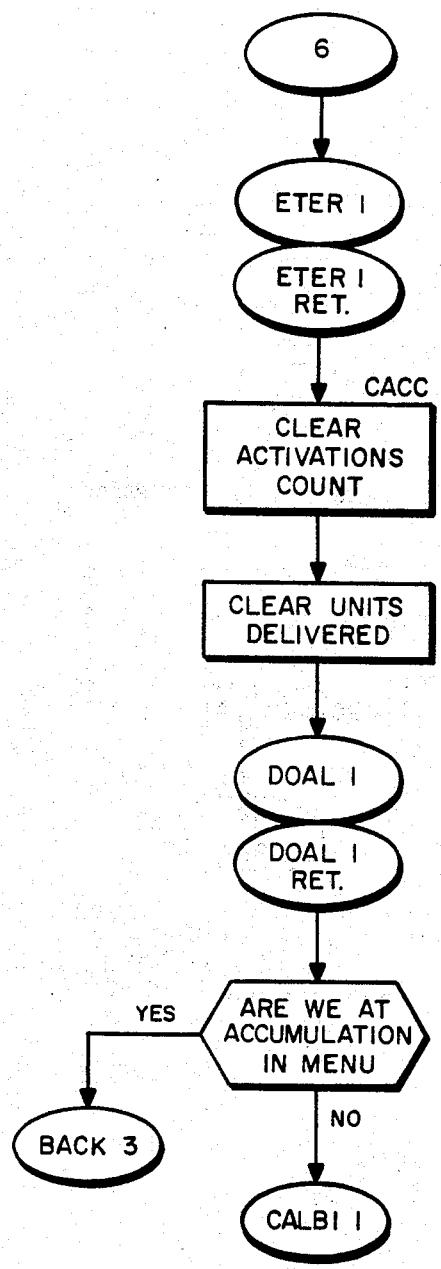
Fig. 5.20

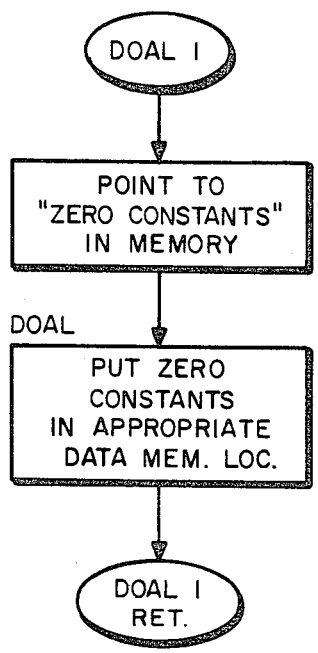
Fig. 5.21
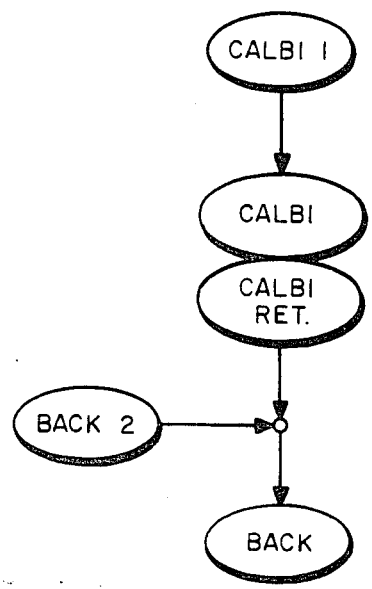
Fig. 5.22

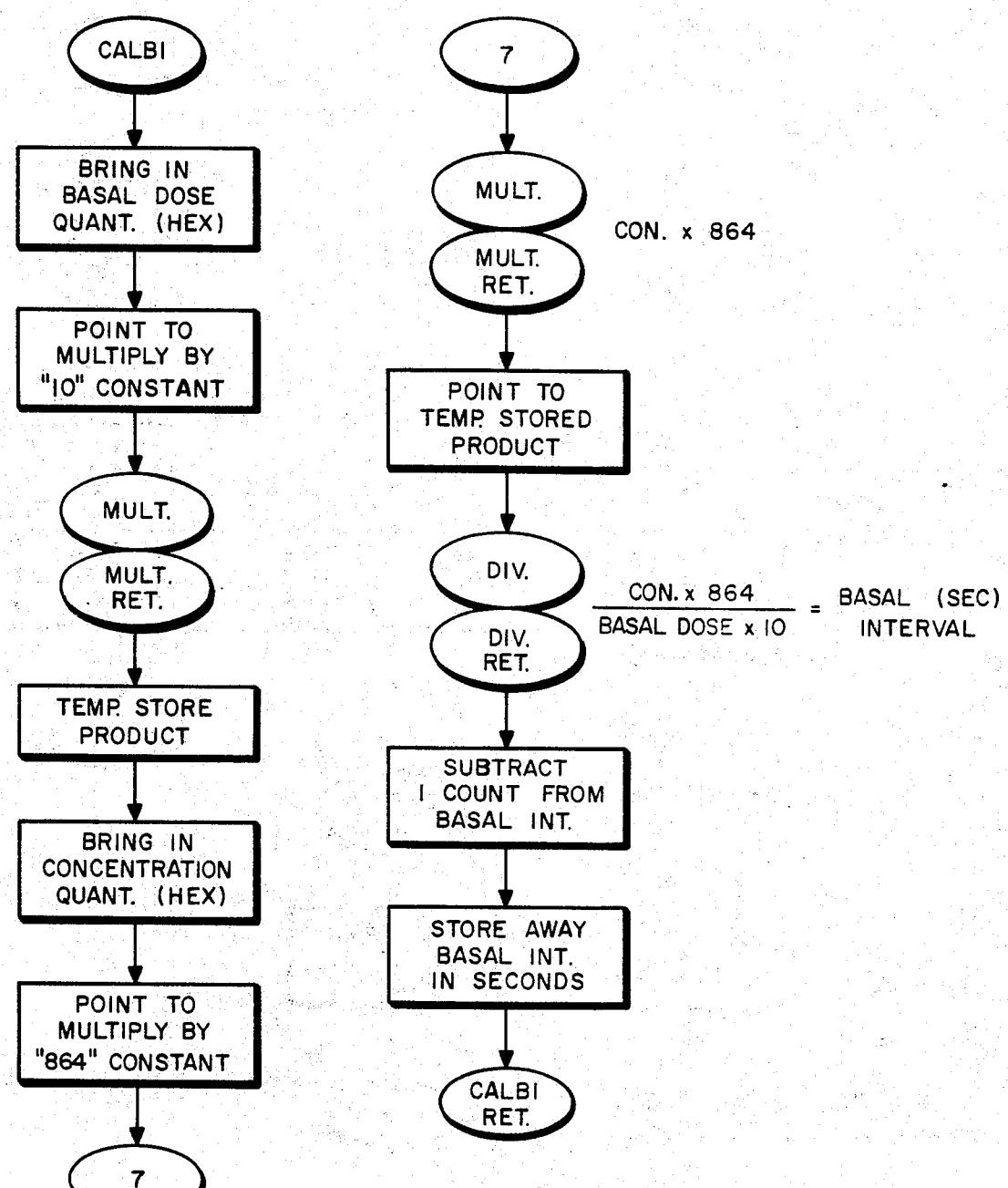
Fig. 5.23
Fig. 5.24

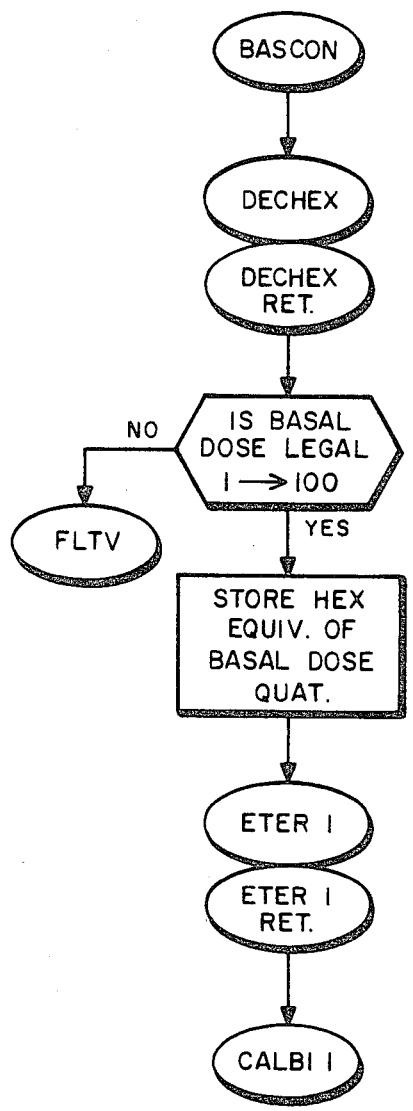
Fig. 5.25
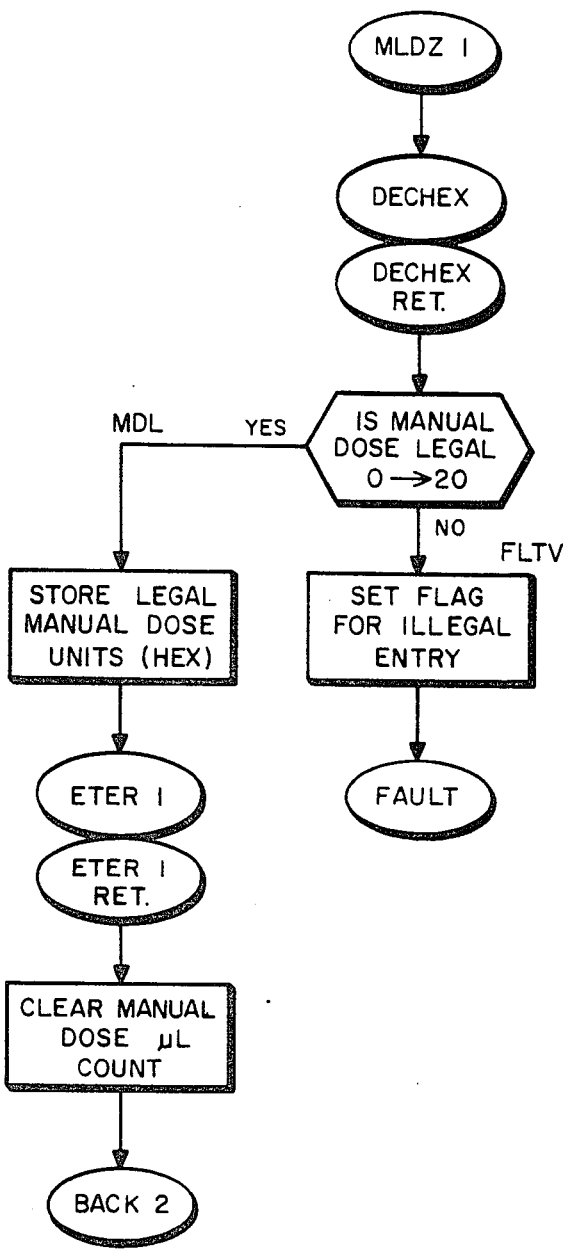
Fig. 5.26

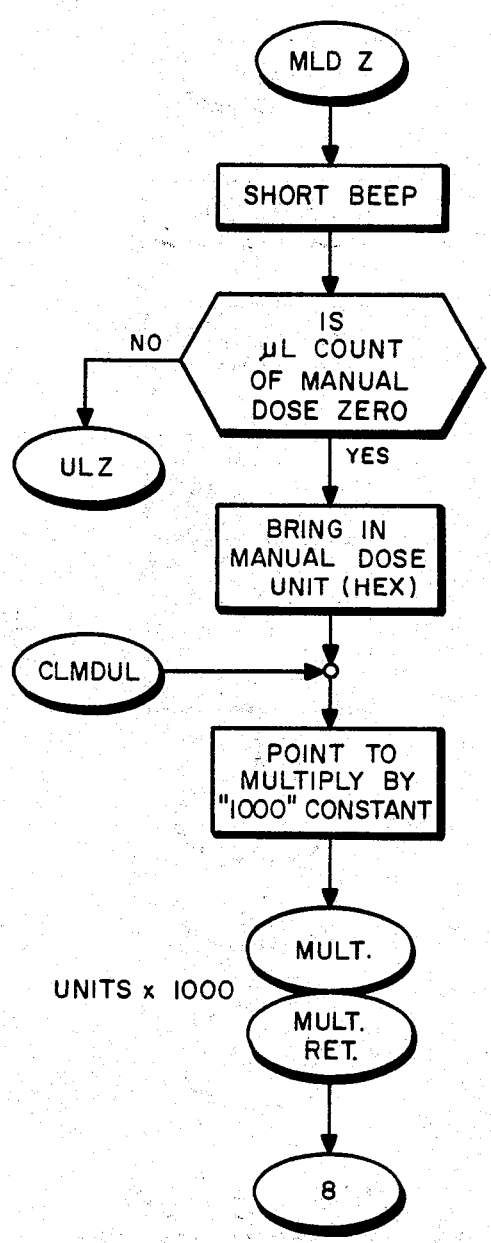
Fig. 5.27
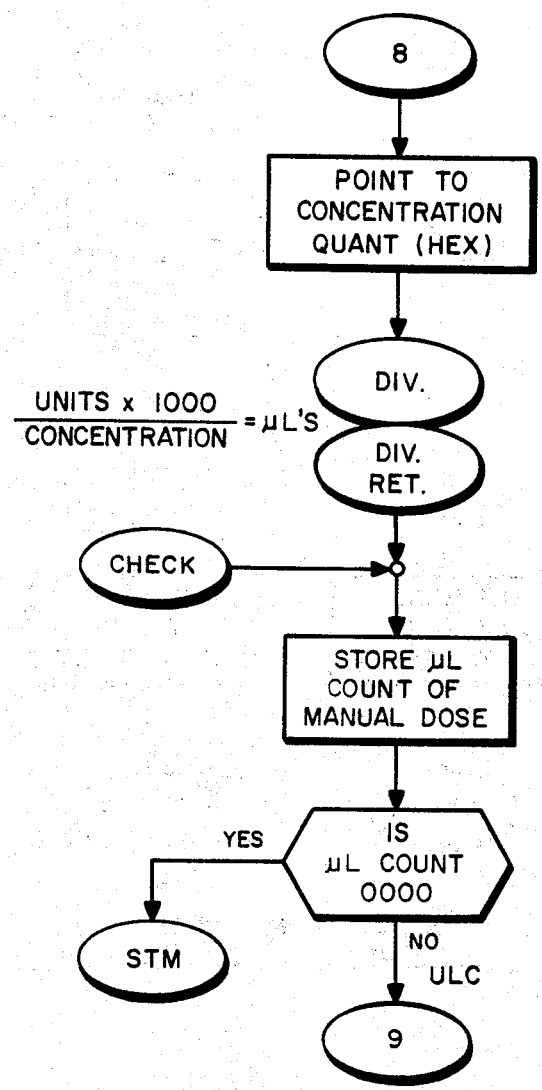
Fig. 5.28

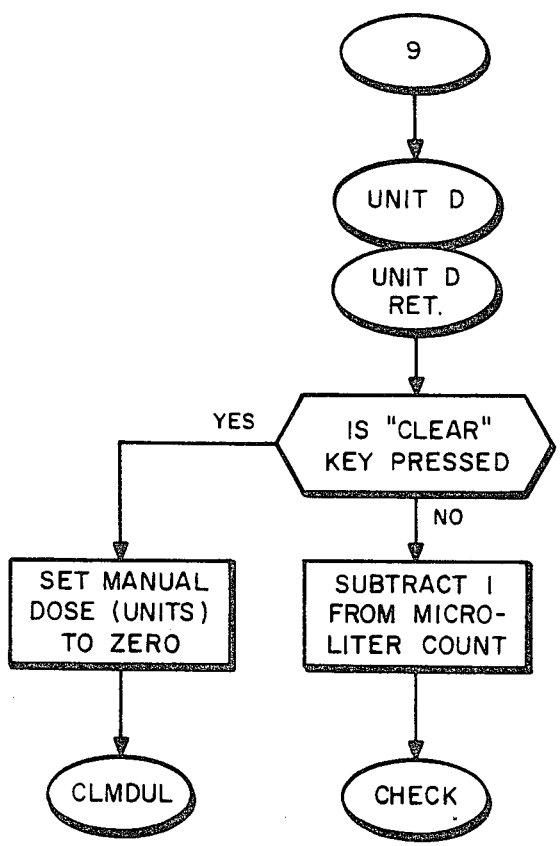
Fig. 5.29
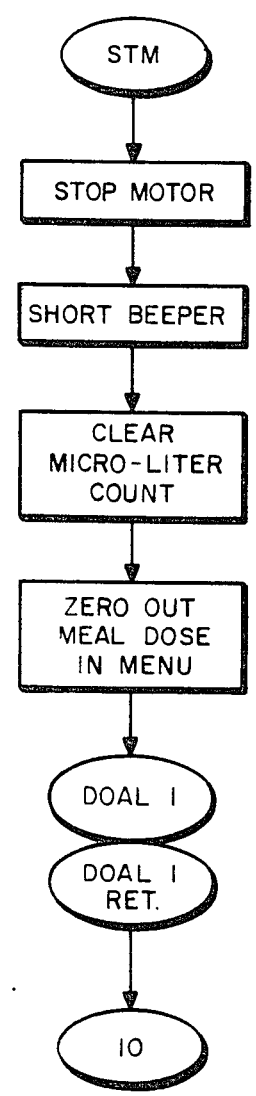
Fig. 5.30

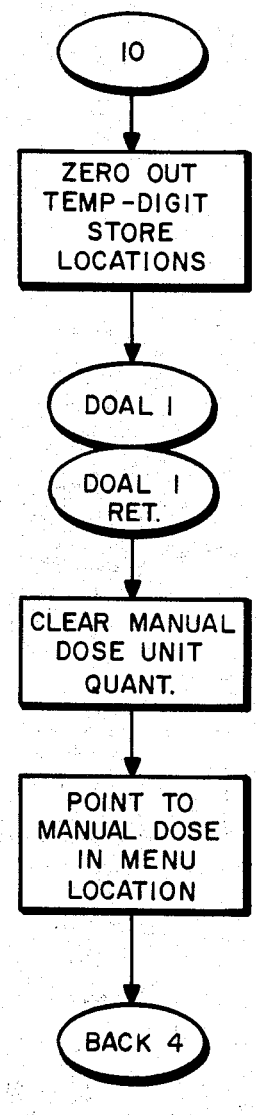
Fig. 5.31
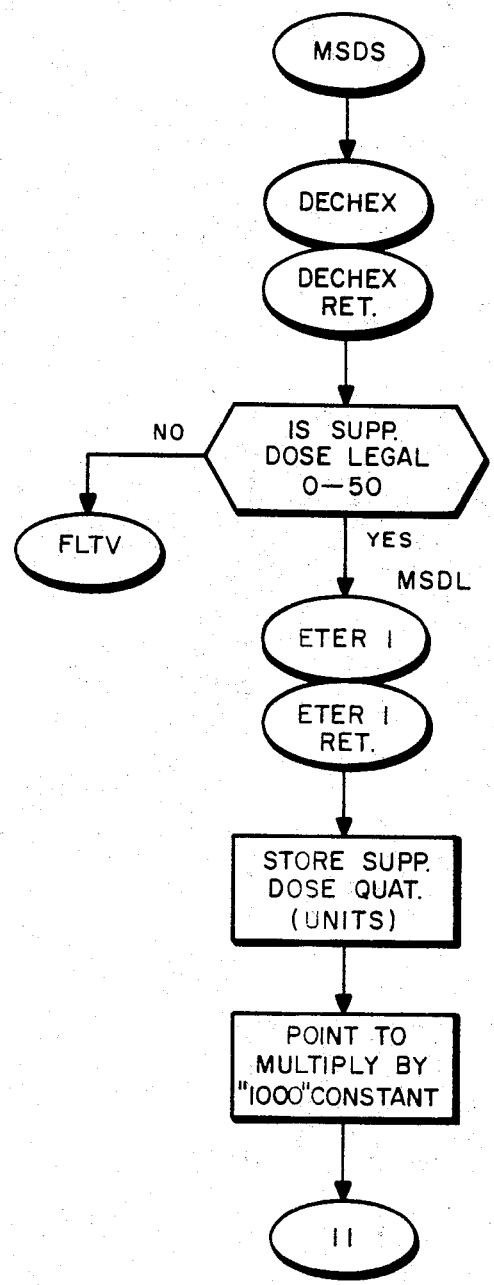
Fig. 5.32

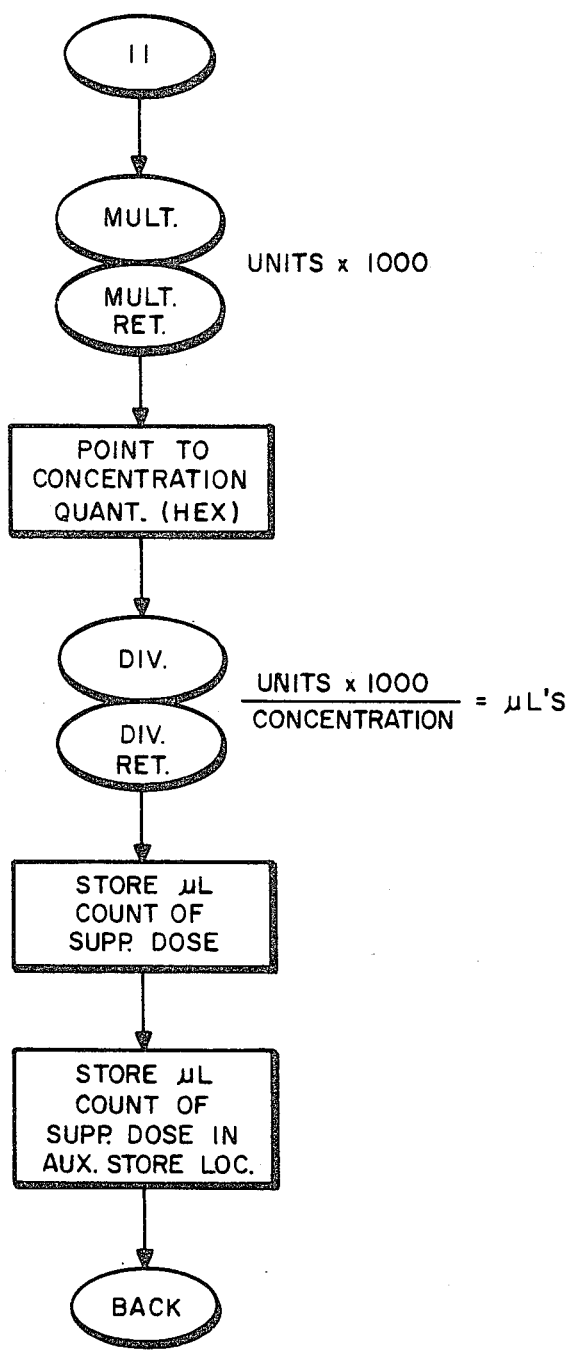
Fig. 5.33
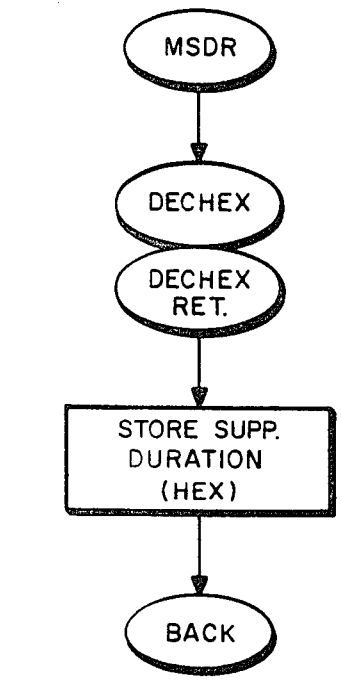
Fig. 5.34

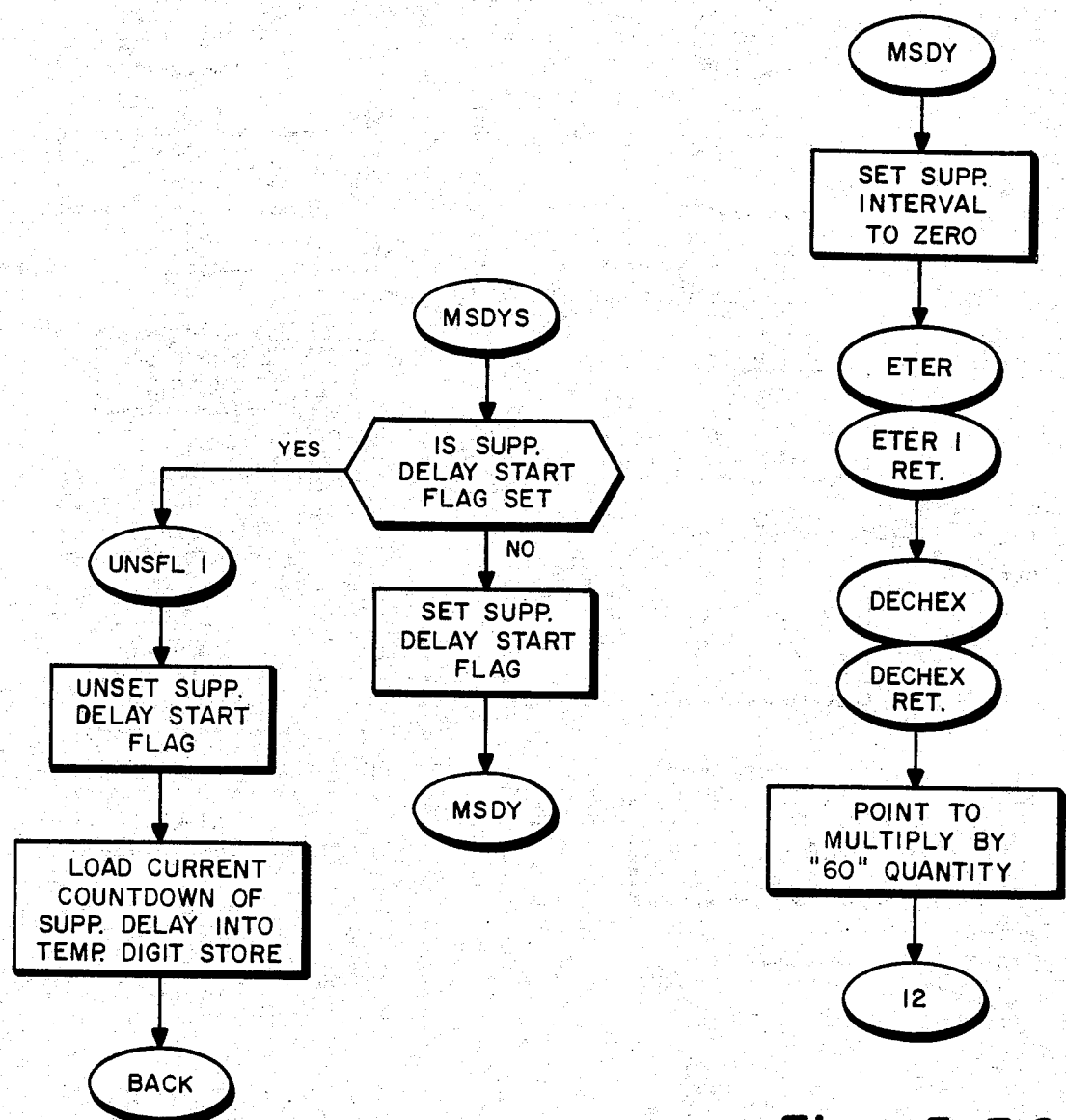
Fig. 5.35
Fig. 5.36

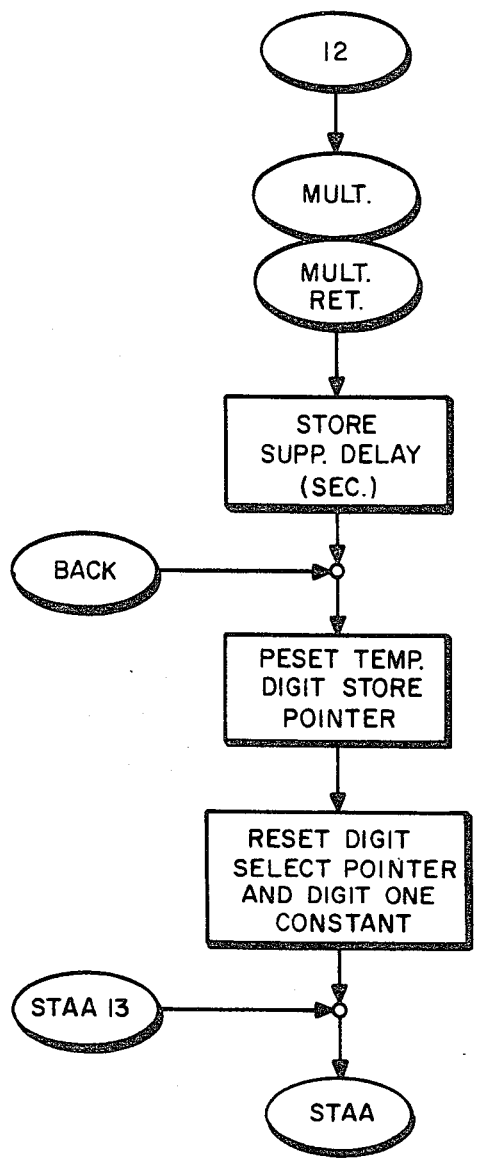
Fig. 5.37
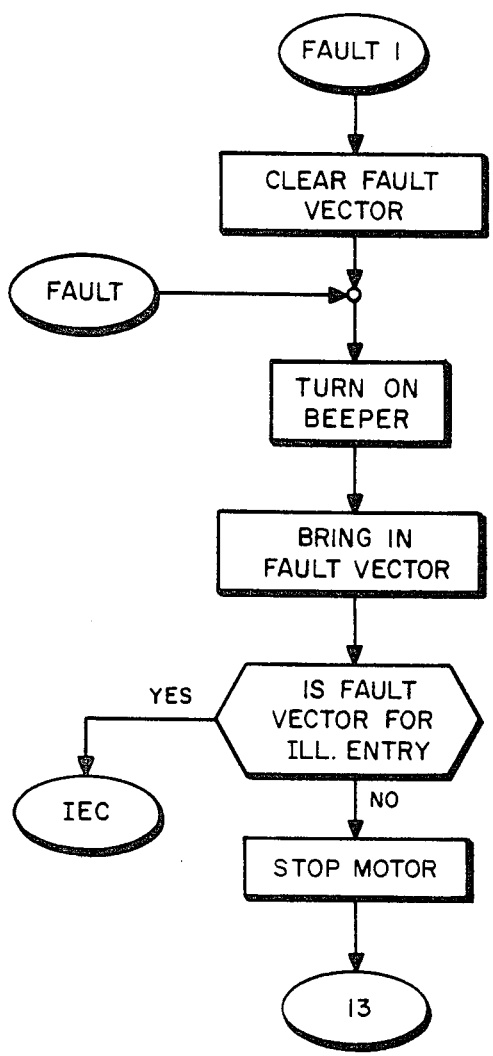
Fig. 5.38

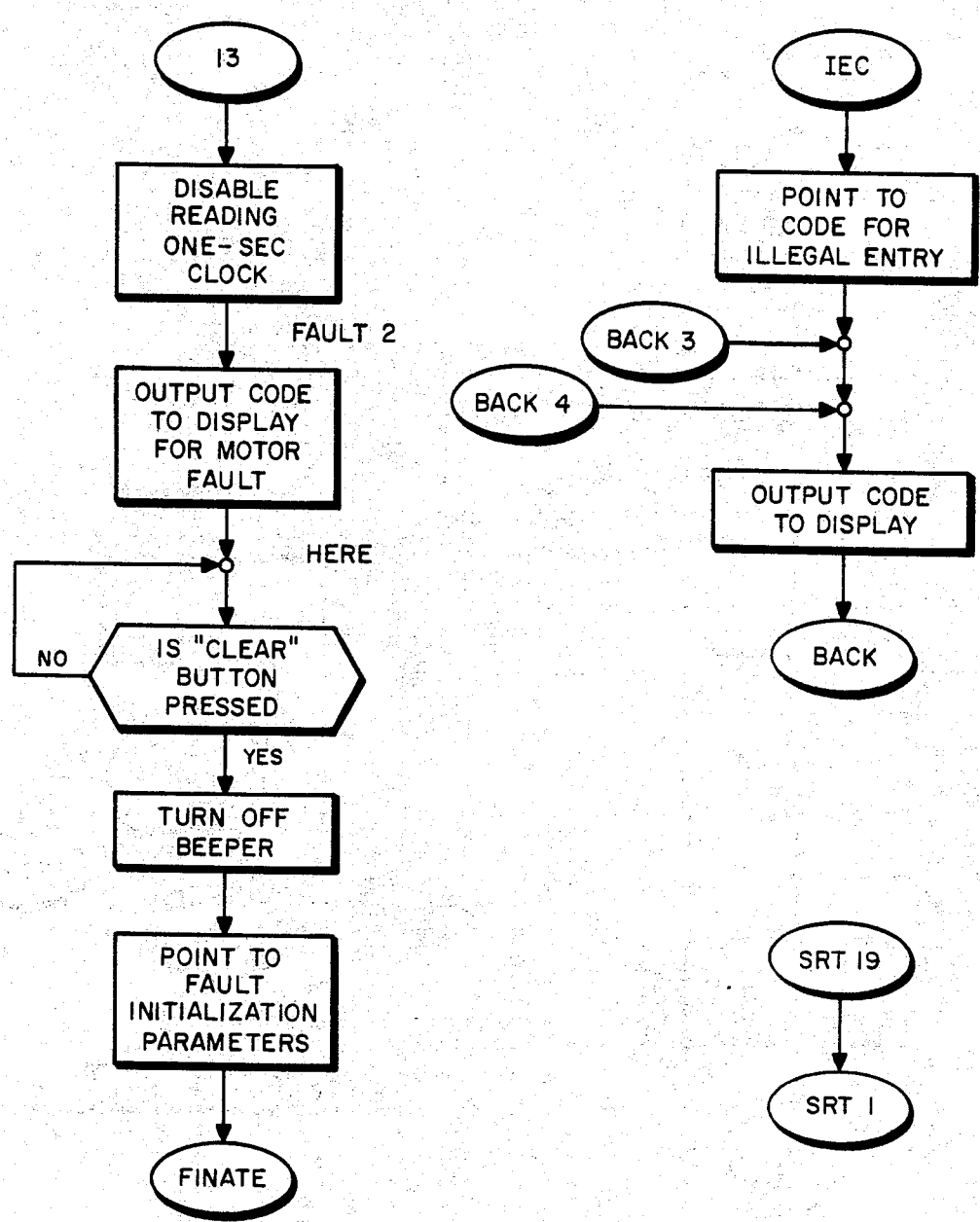
Fig. 5.39
Fig. 5.40

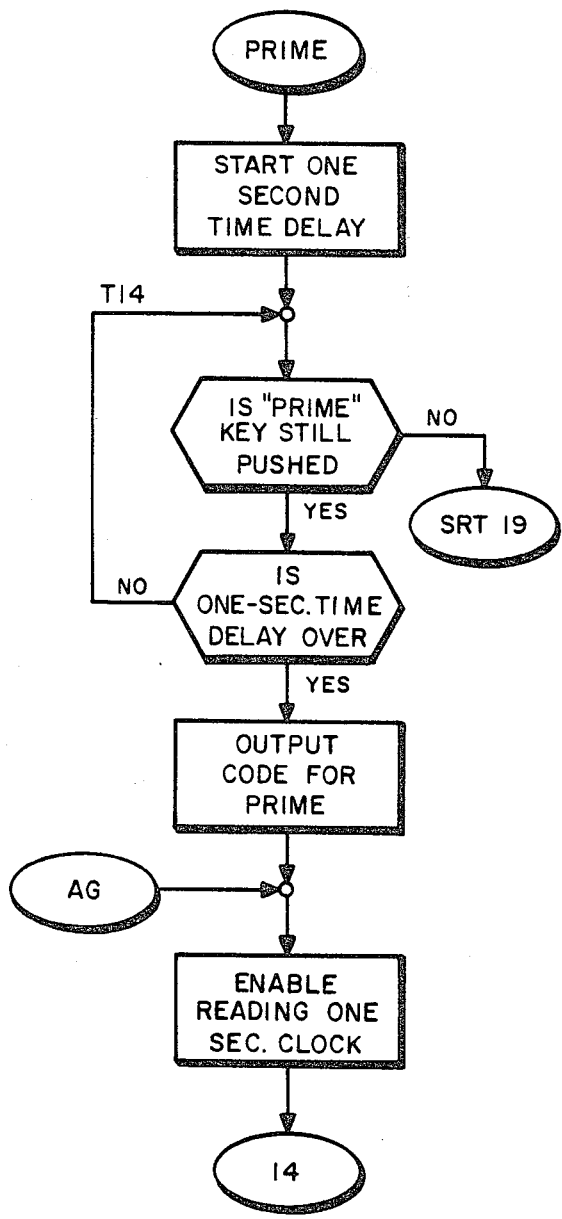
*Fig. 5.41*
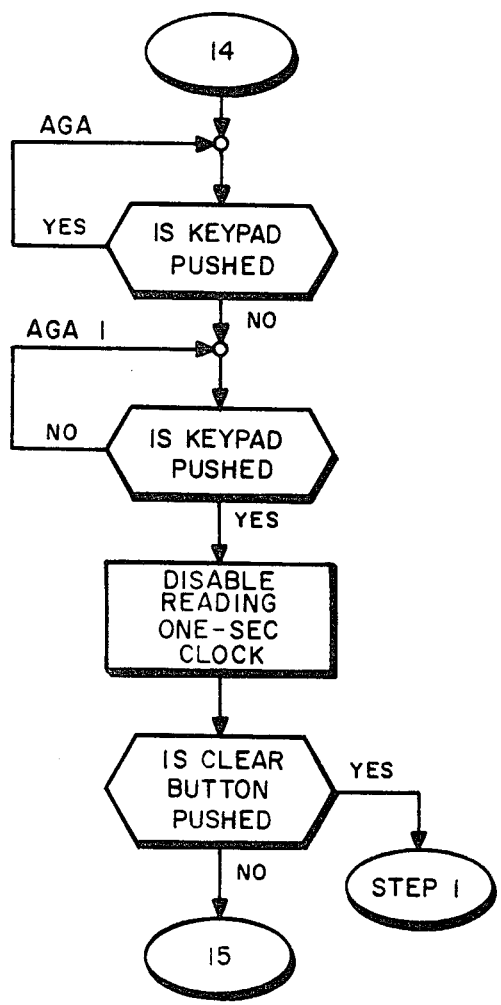
*Fig. 5.42*

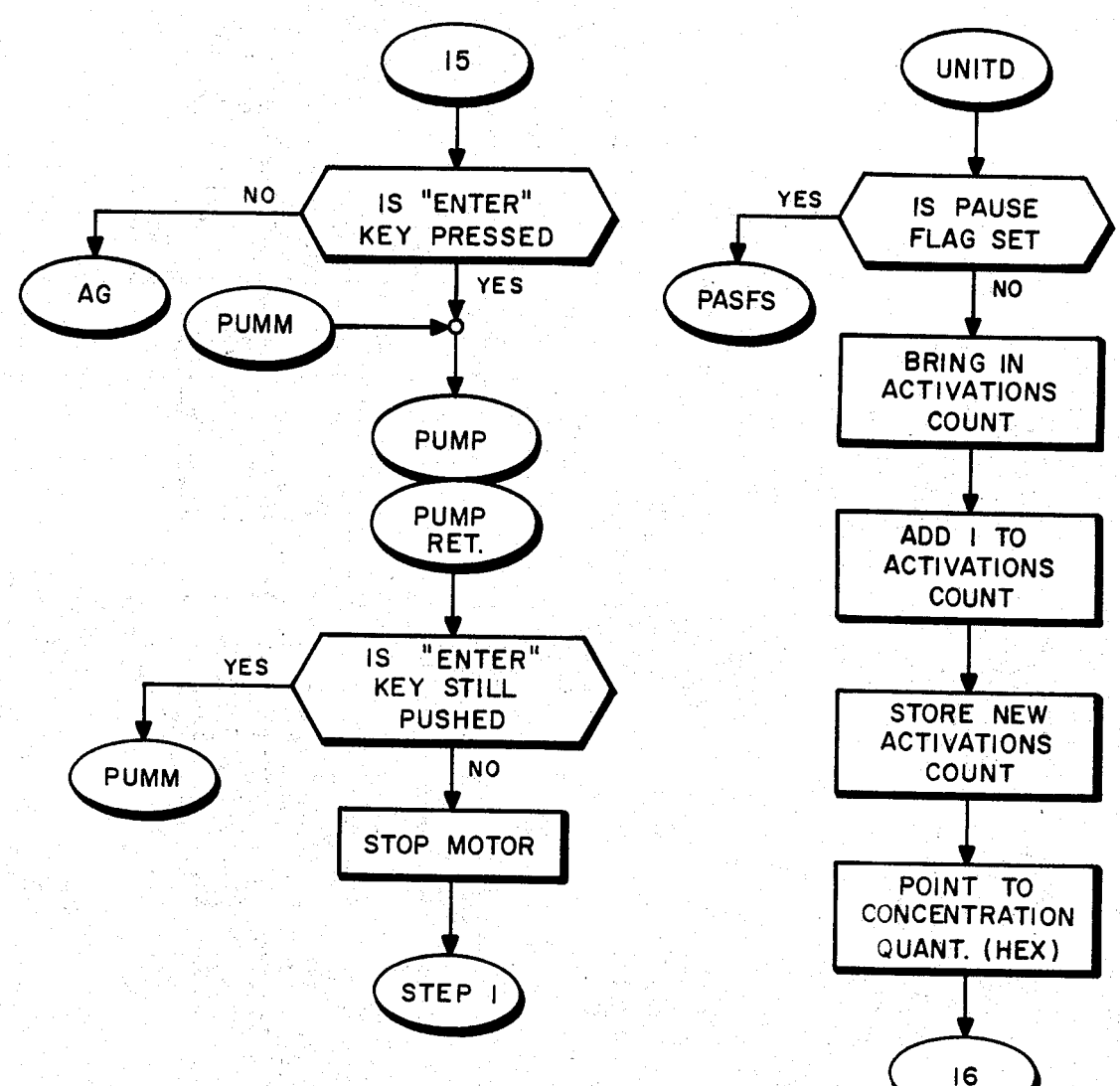
Fig. 5.43
Fig. 5.44

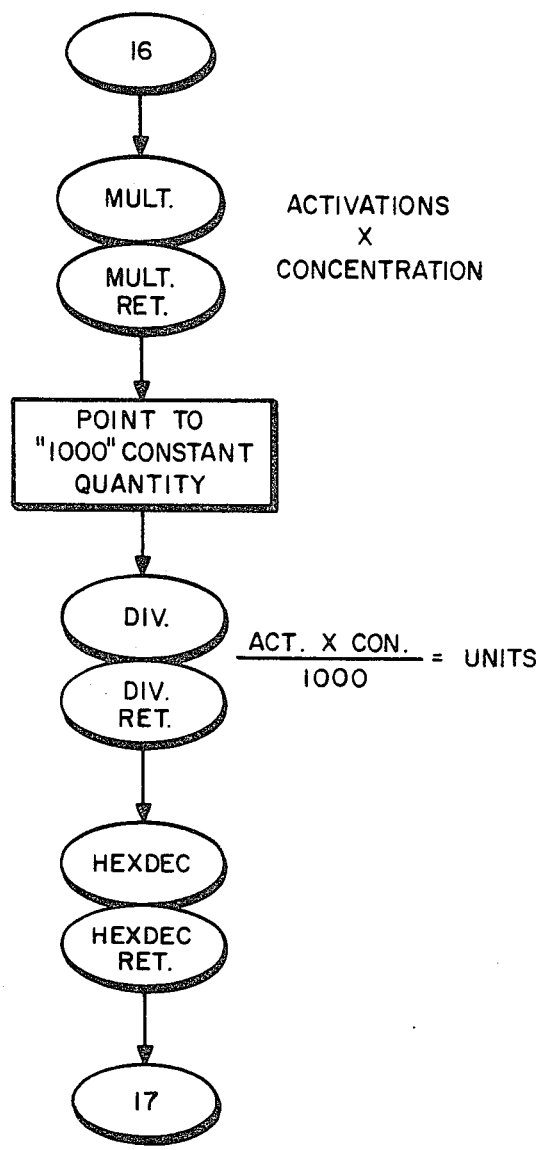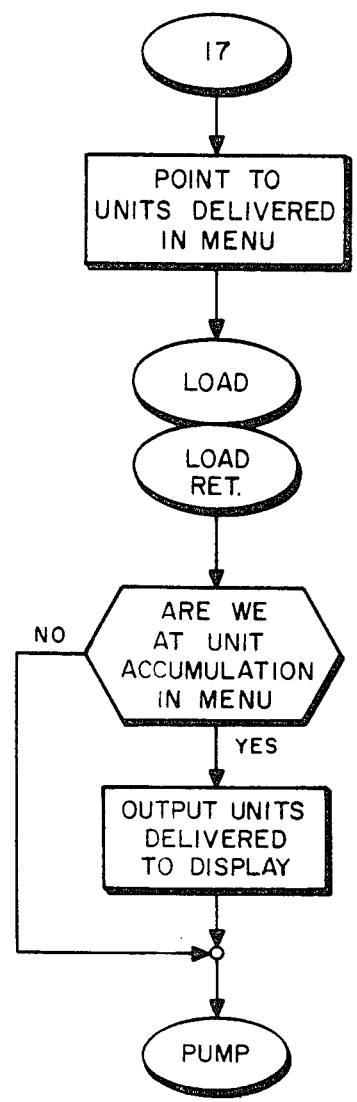
Fig. 5.45
Fig. 5.46

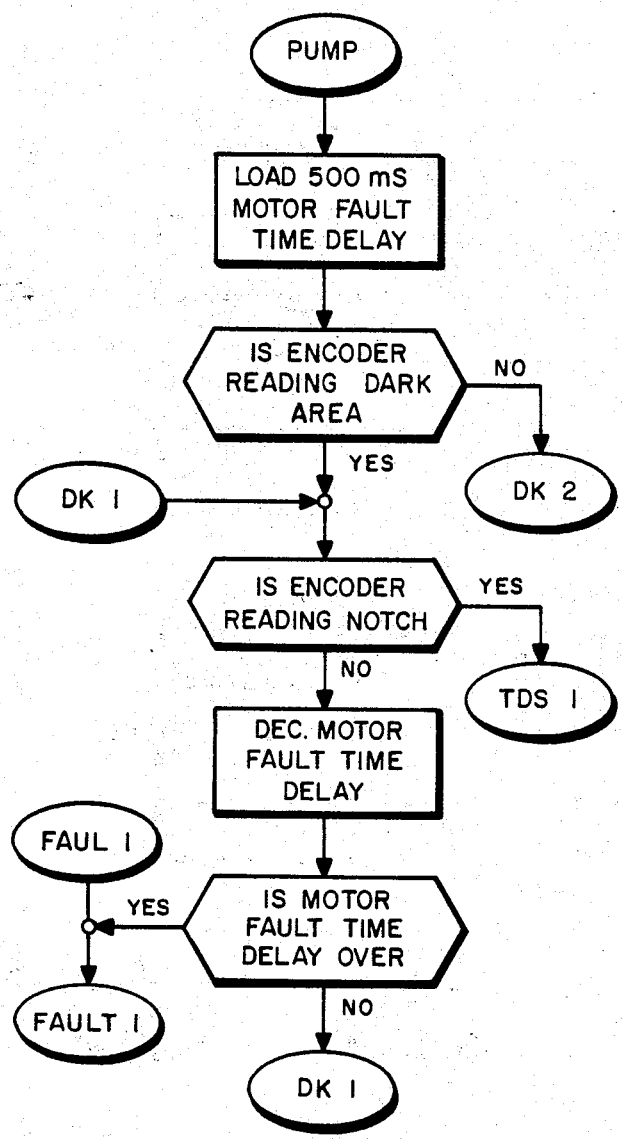
Fig. 5.47
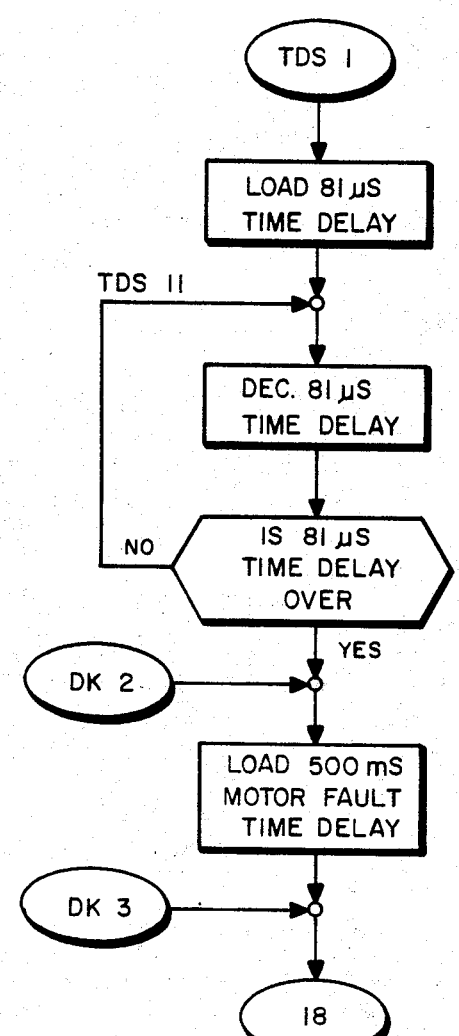
Fig. 5.48

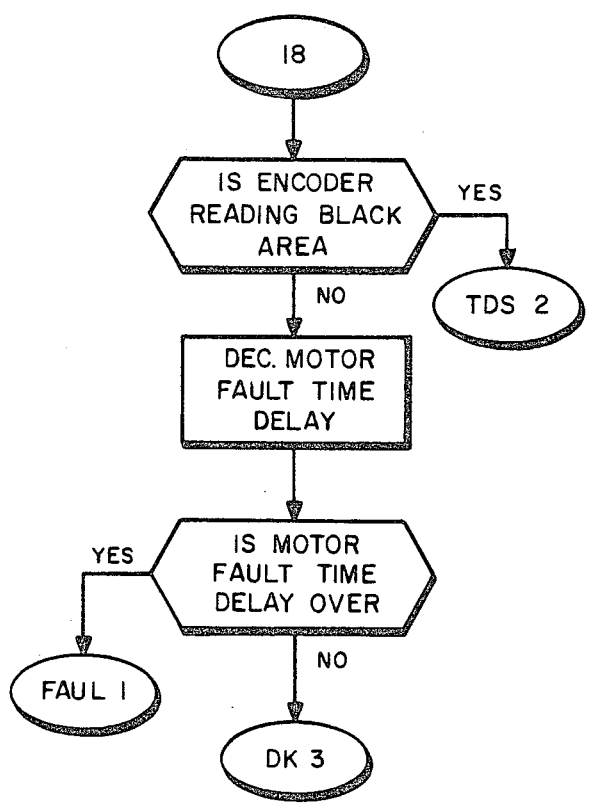
*Fig. 5.49*
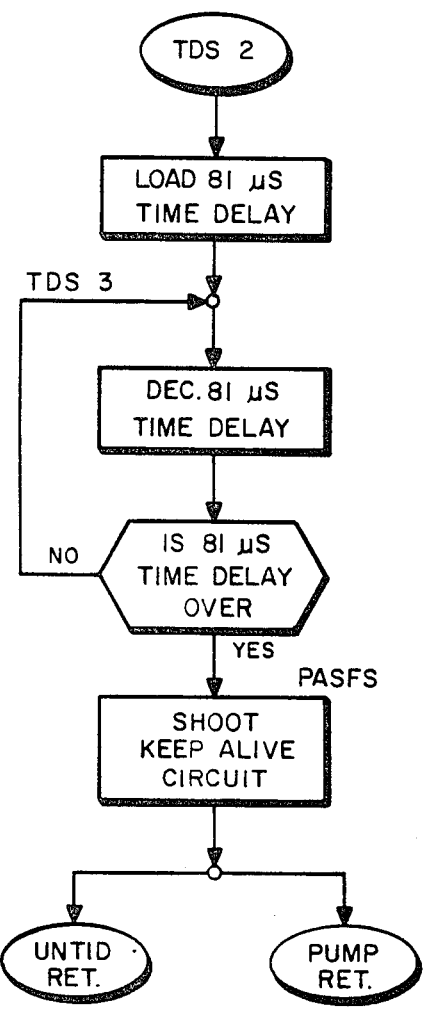
*Fig. 5.50*

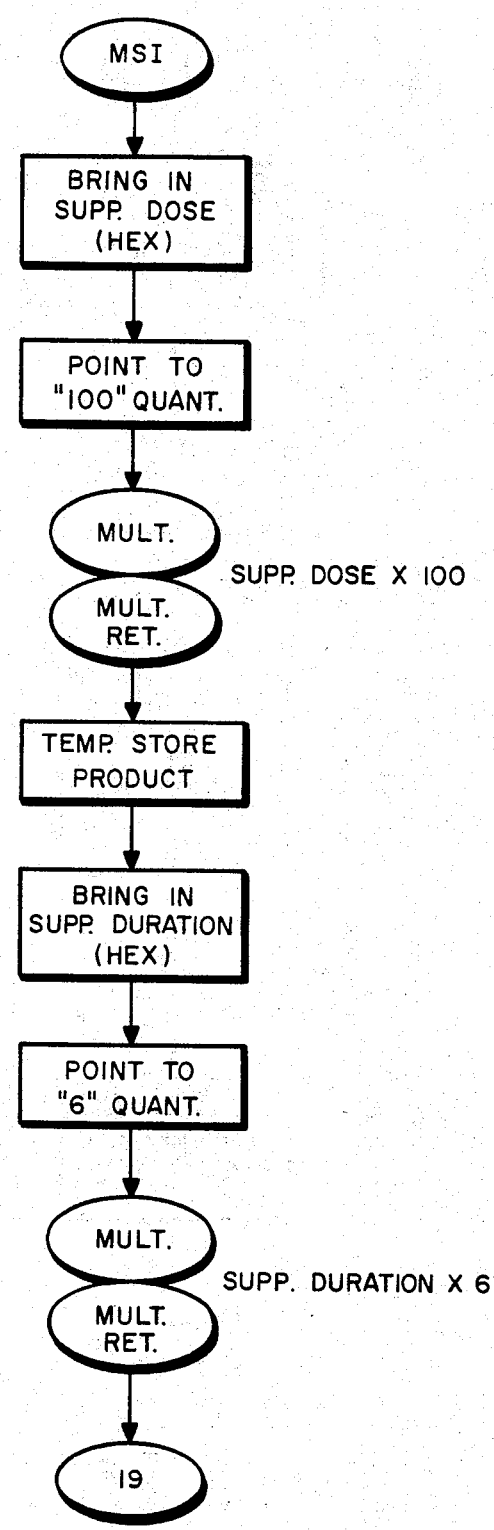
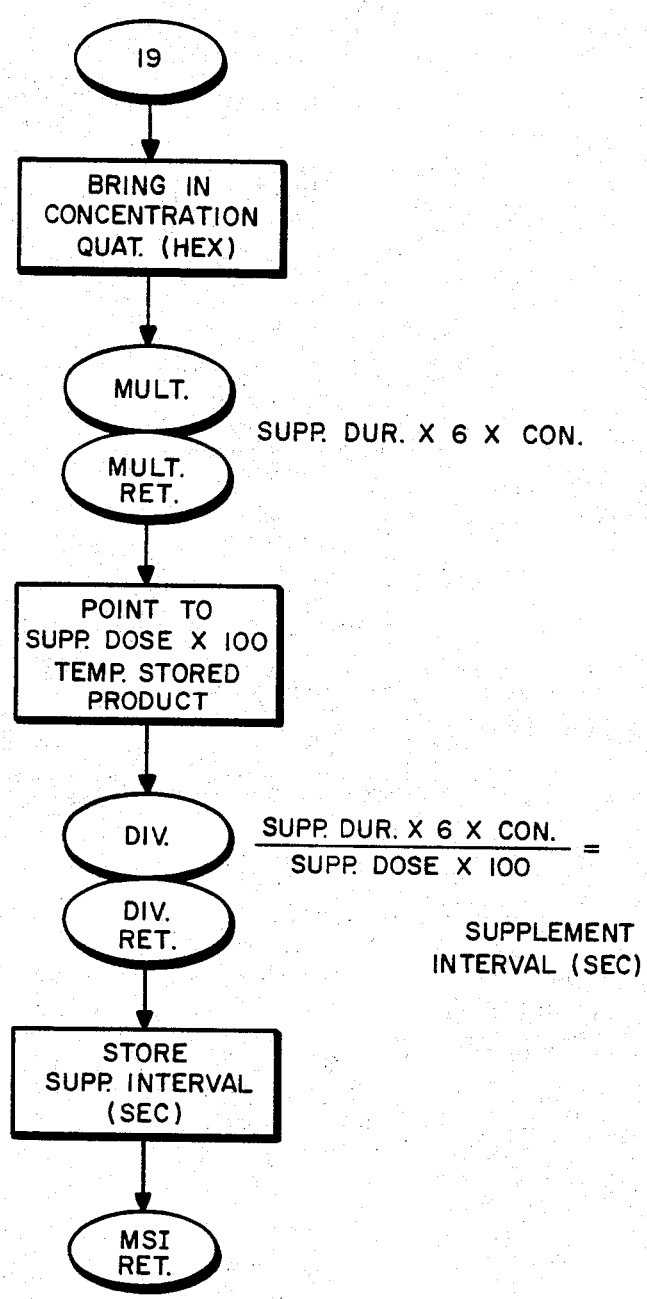
Fig. 5.51
Fig. 5.52

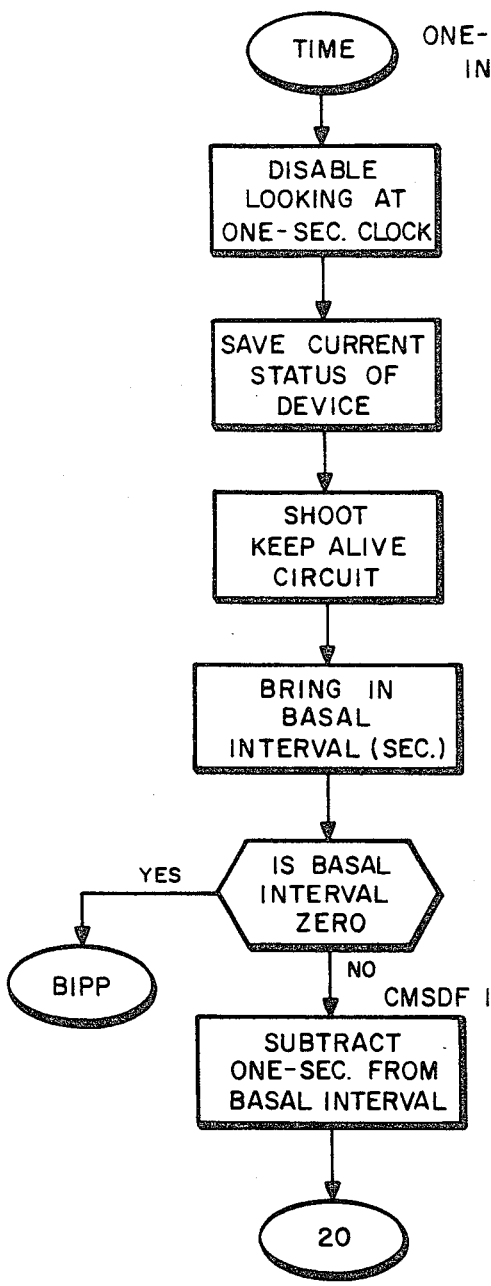
Fig. 5.53
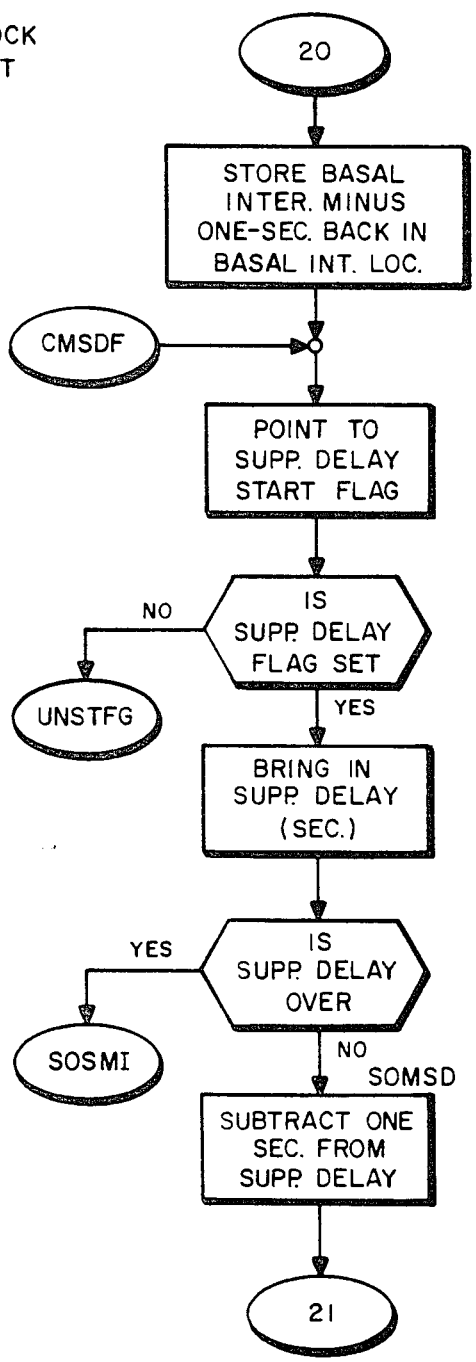
Fig. 5.54

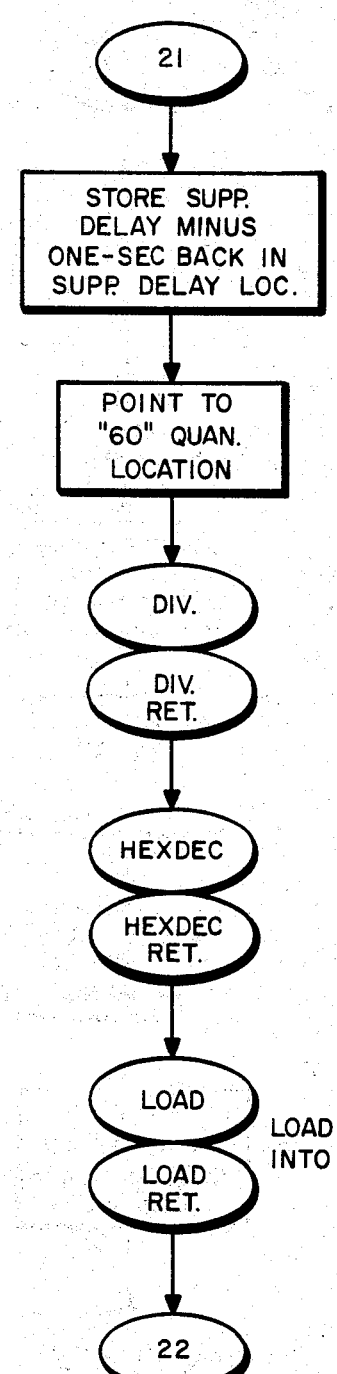
*Fig. 5.55*
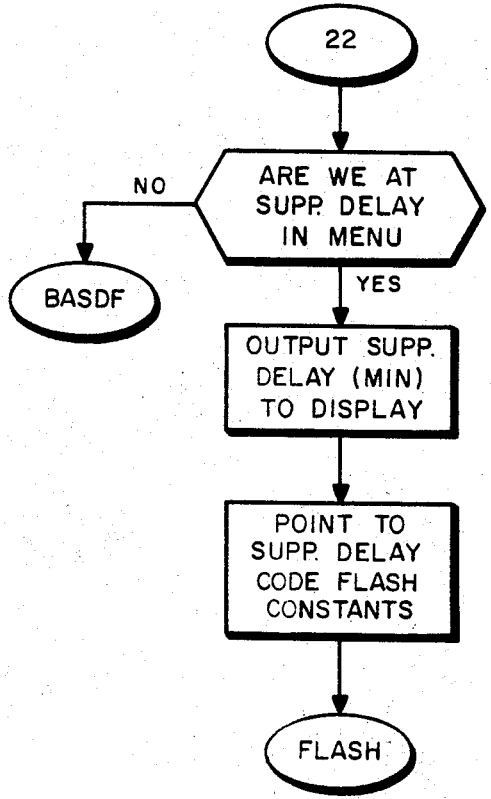
*Fig. 5.56*

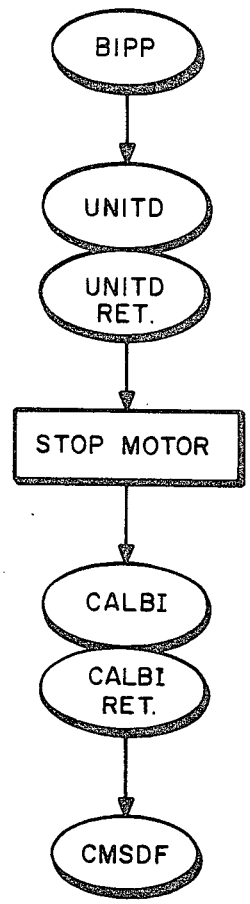
Fig. 5.57
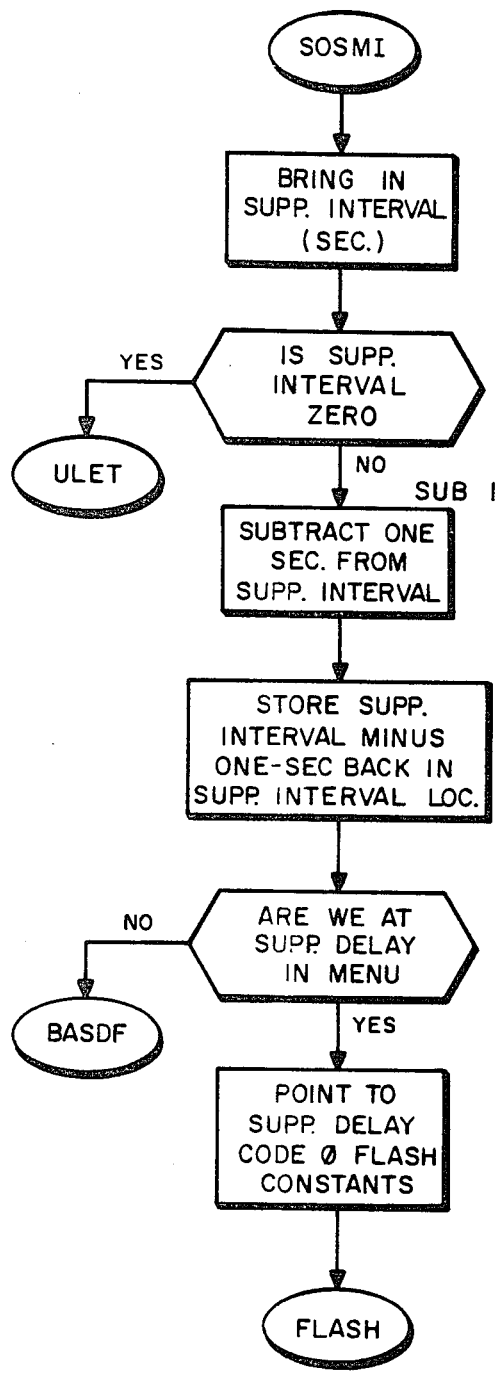
Fig. 5.58

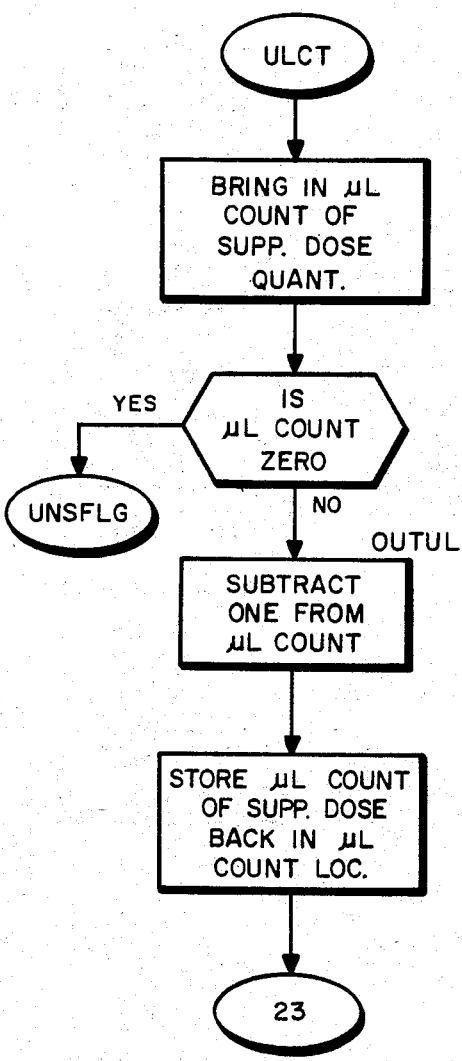
Fig. 5.59
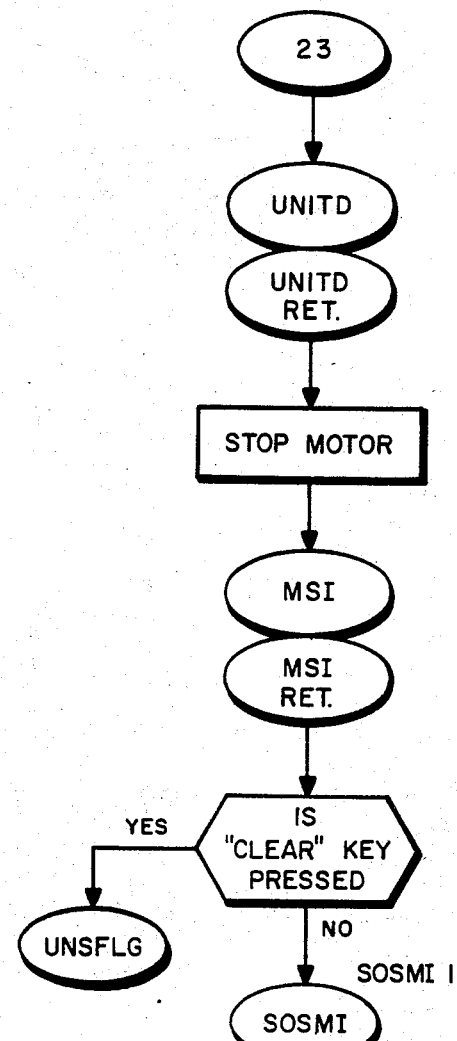
Fig. 5.60

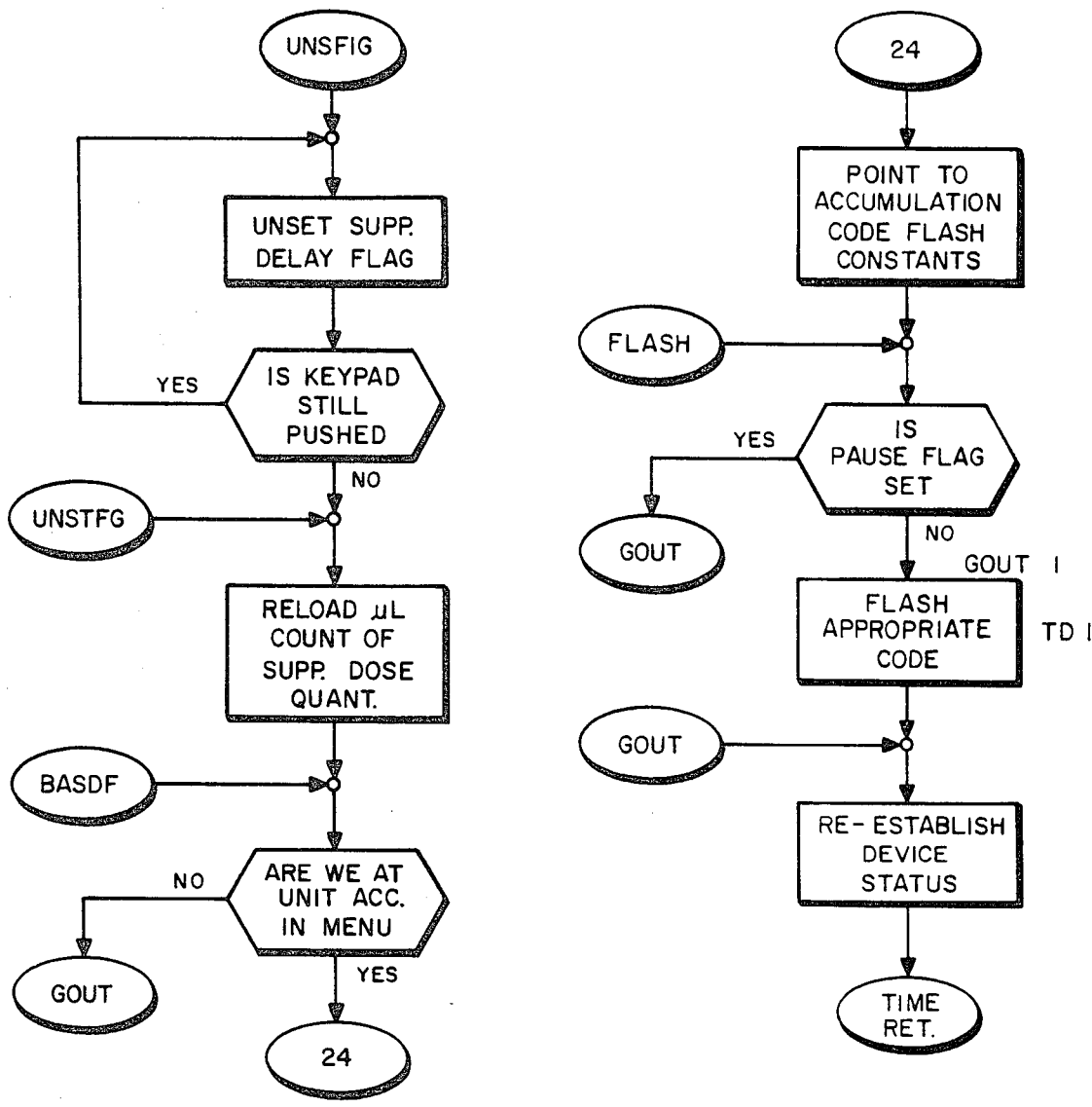
Fig. 5.61    Fig. 5.62

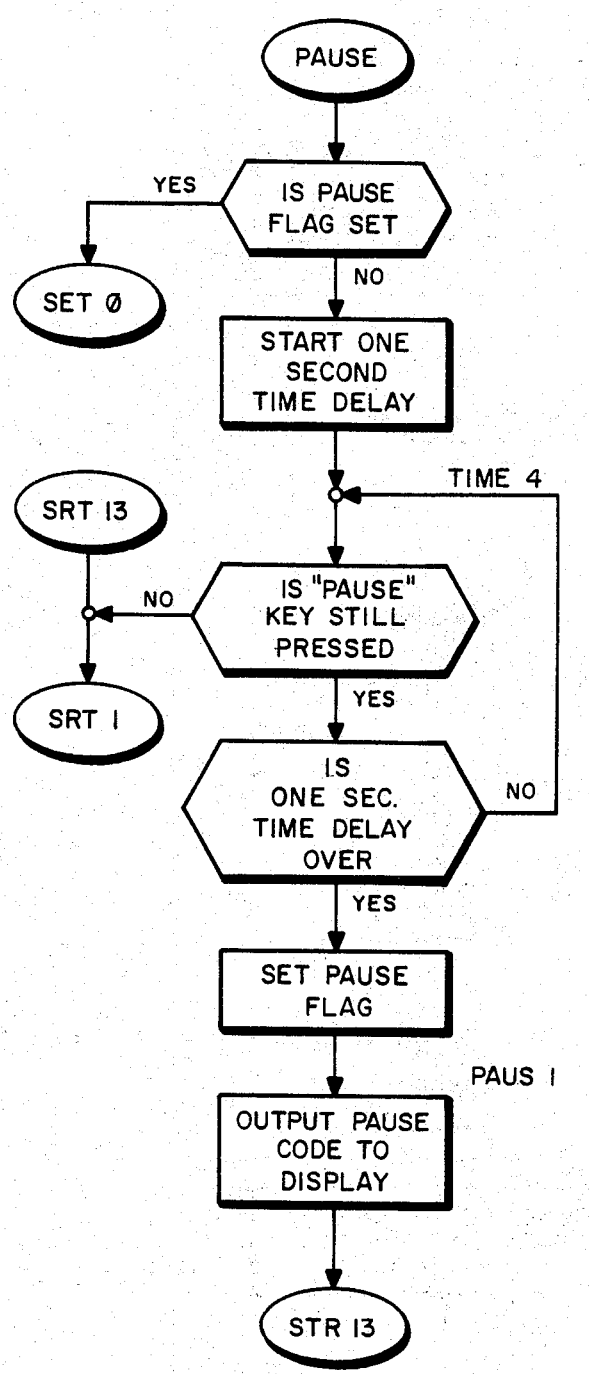
Fig. 5.63
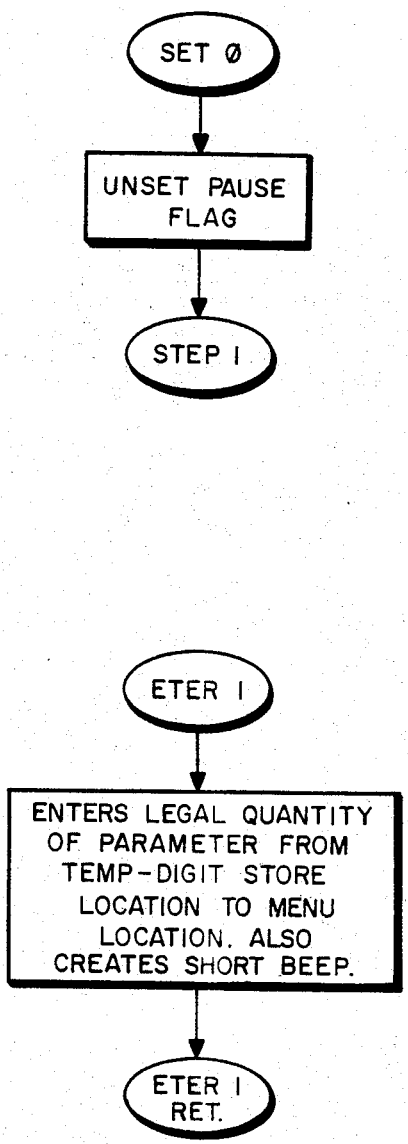
Fig. 5.64

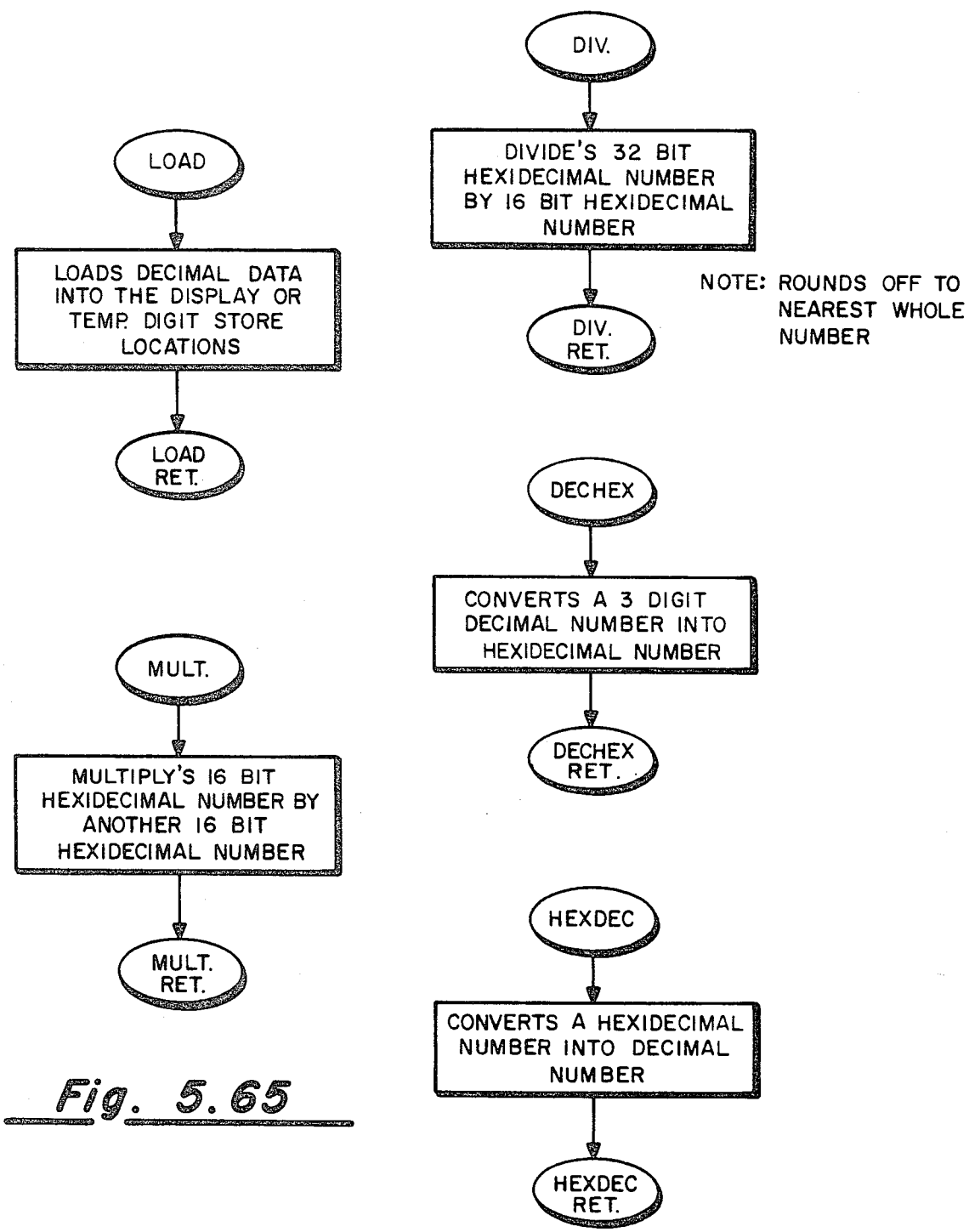
Fig. 5.65
Fig. 5.66

AMBULATORY INFUSION PUMP HAVING PROGRAMMABLE PARAMETERS

BACKGROUND OF THE INVENTION

The present invention relates to infusion pumps and, in particular, to a portable, programmable infusion pump wherein incremental doses of a medicant are delivered at a self-calculated rate and wherein a plurality of modes of operation may be selectively programmed to ensure that a proper total daily profile and dosage is delivered.

Infusion pumps or automatic medicant injecting mechanisms have existed in the prior art for a great many years. Such devices typically comprise a chamber for containing a medicant and means for controllably causing the evacuation of the chamber. Various and sundry control means have been employed and which most typically take the form of electro-mechanical arrangements including motor means, drive means, means for evacuating the chamber and pulse producing means for controllably operating the motor means. Some of the more recent of such systems can be found upon reference to U.S. Pat. Nos. 3,858,581; 4,150,672 and 4,191,187, and which generally show and describe infusion pumps that employ motor means, a transmission system and a lead screw for controllably causing the administration of the doses of the medicant.

In the Whitney U.S. Pat. No. 4,150,672 patent, the medicant is delivered at a rate established in response to individual, fixed width pulses that are produced by an oscillator. Wright in the U.S. Pat. No. 4,191,187 patent also delivers the medicant as per fixed width pulses in response to the actuation/deactuation of a cam and micro-switch that are operatively coupled to the lead screw assembly to control the drive/braking action of the assembly. Kamen in the U.S. Pat. No. 3,858,581 patent, on the other hand, recognizes that uniform pulses are not the same as the uniform displacement of the syringe plunger, due to the number of factors that affect the dosage delivered (i.e. variations in the work load, supply voltage and medicant). Accordingly, Kamen discloses the use of a cam/micro-switch and counter assembly for uniformly displacing the syringe plunger as each dose is delivered to the patient.

Efforts employing digital techniques can also be found upon reference to Franetzki et al in U.S. Pat. No. 4,282,872 and Ellinwood in U.S. Pat. No. 3,923,060. Franetzki generally discloses partially implantable apparatus employing preprogrammed sequences that deliver a selected amount at a rate pursuant to the programmed sequence. Ellinwood, on the other hand, discloses an implantable infusion device that employs a microcontroller that operates in response to a plurality of sensors contained within the body. The pump then dispenses the medicant in accordance with a pre-stored program that is entered either upon implant or via an external programmer.

Nowhere, however, does the prior art disclose the present apparatus and which generally comprises a portable, programmable infusion pump that acts to dispense uniform incremental doses of medicant at a rate determined by the desired dose and concentration, programmed by the patient or doctor. In its preferred embodiment, the present infusion apparatus employs a lead screw along with photo coupling means and a counter for determining the volume of each incremental dose. The number and rate of application of the doses is then determined by the microprocessor, upon entering the concentration and rate.

The above features and advantages of the present invention, as well as further objects thereof, will however become more apparent and more fully appreciated upon reference to the following description and drawings.

BRIEF DESCRIPTION OF THE DRAWINGS

FIG. 2 depicts the motor means and transmission assembly for coupling the rotational movement of the motor means to the lead screw.

FIG. 3a shows another view of FIG. 2, but wherein the slotted wheel and photo-coupled encoder assembly can be seen more clearly.

FIG. 3b is a detailed view of the slotted wheel that produces the pulse train that ensures the proper volume of medicant is delivered with each incremental dose.

SUMMARY OF THE INVENTION

A portable, programmable infusion pump, wherein the infusion pump comprises a chamber for containing a medicant, means for controllably expelling the medicant from the chamber into a patient requiring the medicant and means for programmably calculating the total number and rate at which each incremental dose is delivered, upon programming the desired dosage and medicant concentration. The control means also includes a photo-coupled assembly for producing a plurality of pulses which, in turn, are counted to ensure that the proper incremental volume of medicant is delivered with each dose.

The apparatus also permits the delivery of a supplemental dose, pursuant to a programmed delay interval, a programmed supplemental dose and a programmed supplemental duration parameter. The supplemental dose thus corrects where insulin is the medicant for the hypoglycemic reaction that is often experienced after a period during which an insufficient dosage has been delivered.

The infusion pump further permits programming a manual dose, priming the means for delivering the medicant, maintaining a record of the total accumulated dose delivered between battery changes, audibly warning the user if an error condition is detected and programming a lock-out function.

DESCRIPTION OF THE PREFERRED EMBODIMENT

Figure 1:
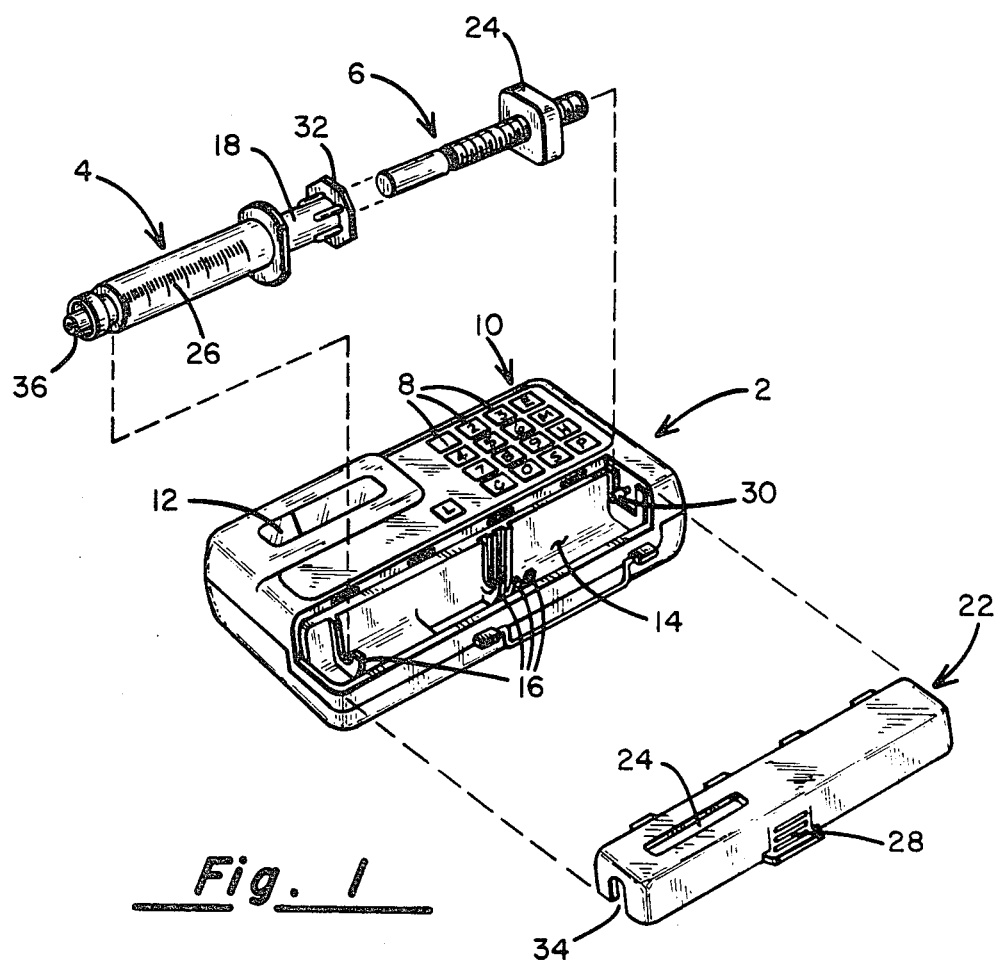
FIG. 1 shows an exploded view of the present apparatus wherein the syringe, plunger and lead screw are shown relative to their placement within the medicant compartment.

Referring to FIG. 1, an exploded view is shown of the container 2 that contains the medication holding syringe 4 and the lead screw 6 that together generally comprise the pump of the present invention. Mounted in the upper right hand corner of the front surface of container 2 are a plurality of keys 8 that are attached to separate membrane switches and which keys collectively comprise the keyboard 10 by which the present invention is programmed.

The keyboard 10 permits an operator to address the various parameters which control the pump and to enter the specific dose data that determines the rate of delivery. The necessary numerical values for each programmable parameter are entered via the numerical keys 0 through 9. The remaining keys then control the commands corresponding to the: E(ENTER); M(MANUAL); H(HOLD); P(PRIME); S(STEP); C(CLEAR); and L(LOCK-OUT) functions.

Mounted in the upper left hand corner of container 2 is a liquid crystal display (LCD) 12 and by which the operator is able to visually confirm "what" and "if" data is entered as the keys 8 are depressed. It is to be noted the information content of the LCD display 12 is separated, via the solid slashed line so that upon programming, the function code appears to the left of the slashed line while the numerical dose data for that function appears to the right of the slashed line. During the prime and hold functions however, numerical data is not displayed, and in lieu thereof either the P or the H mnenonic is displayed, but which functions will be described in greater detail hereinafter.

The inner shape of the medicant compartment 14 can also be seen in detail, upon reference to the container 2. In particular, it is to be noted that the compartment 14 contains a plurality of support fins 16 that are used to support the syringe 4 at the appropriate height relative to the container 2, as well as limiting the travel of the plunger 18 and drive nut 24.

The medicant compartment 14 is covered, during use, by the cover 22 and which contains a viewing window 24. The medicant compartment, as mentioned, contains the disposable syringe 4, such as a CPI/Lilly Model 9110. During use, the syringe 4 can then be monitored via the viewing window 24, which permits the user to visibly monitor the contents of the syringe 4 and which window is positioned so that the markings 26 on the syringe are visible therethrough. Thus, a user, from time to time, can monitor the amount of medicant that remains within the syringe. The compartment cover 22 is also formed so that it is easily removed from the container 2 by depressing the ridged thumb latch 28.

Referring now to the more detailed view of the syringe 4, the plunger 18, lead screw 6 and drive nut 24 can be seen more clearly in their relative relationships to one another and the hexagonal drive pin 30. Generally, the displacement of the plunger 18 is controlled via the lead screw 6 and drivenut 24, which abuts the flattened end 32 of the plunger 18, and it is the linear displacement of the drivenut 24, via the turning of the lead screw 6, that causes the corresponding displacement of the plunger 18 and the delivery of a volume of medicant that is indicated by the incremental gradations 26 marked on the side of the syringe 4.

The lead screw 6 is typically fabricated so as to have a threaded portion and a non-threaded portion. The threaded portion is typically fabricated with forty threads per inch and which translates into a linear displacement of 0.025 inches per revolution of the lead screw 6. Further, the drive nut 24 is formed so as to partially support the lead screw 6 relative to the plunger 18 and thus move along an axis that is approximately coincident with the syringe 4 and the lead screw 6. The lead screw 6 also contains a hexagonal recess (not shown) within the end of the threaded end thereof for receiving the hexagonal drive pin 30, so that upon the rotation of the head screw 6, via the drive pin 30, the drive nut 24 will move linearly to the left (with respect to the drive pin 30) and thereby cause the plunger 18 to eject the medicant from the syringe 4. It should also be noted that the plunger 18 has a hollow formed through the flattened end 32 so as to receive the unthreaded portion of the lead screw 6 and maintain contact between the drive nut 24 and the plunger head 32 as the drive nut 24 moves along the lead screw 6.

From FIG. 1, it should also be noted that an opening 34 is formed in the side of the compartment cover 22 so as to permit the coupling of a tube (not shown) therethrough with the luer connector 36 of the syringe 4. The tube in turn, is coupled to a needle assembly that is affixed to the patient at most typically the thigh or abdomen so as to deliver the doses subcutaneously. The tube is also typically taped to the patient's skin and beneath the patient's clothing so as not to be visible during use.

Referring next to FIG. 2, a detailed view can be seen of the drive assembly that is contained within the container 2, beneath the keyboard 10. The drive assembly is generally comprised of a motor 50 that is attached to a gearbox 52, a pinion shaft 54, a plurality of gears 56, 58 and 60, and a drive shaft 62, all of which are mounted in a chassis 64. The pinion shaft 54 is coupled on one end to the gearbox output shaft 66 and a bearing journal 68 on the other end fits in a sintered bronze bearing 70 which is press fitted into the chassis 64. One end of the pinion shaft 56 is also machined to provide the gear teeth 56. The drive gear 60 is similarly supported by the sintered bronze bearings 78 and 80. The idler gear 58 is supported by and revolves freely on a shaft which is press fitted in the chassis 64. Thus, rotation of the output shaft 66 causes the pinion shaft 54 to rotate and, in turn, the idler gear 58 and drive gear 60. The pinion shaft 54 has 13 teeth, and the drive gear has 49 teeth, which together produce a critical gear train, that will be described in greater detail hereinafter.

The drive gear 60 assembly differs slightly in that a bushing 80 is passed through the bracket 64 so that the output shaft 62 and the hexagonal drive pin 30 can freely rotate therein. It is to be noted that the hexagonal drive pin 30 is formed from the cylindrical output shaft member 62. The hexagonal drive pin 30 thus engages the lead screw 6 within the recess formed therein (not shown) and which is of a corresponding shape, and whereby the leadscrew 6 is free to articulate about the hexagonal drive pin 30.

Thus, the motor 50 upon being subjected to appropriate electrical pulses, translates the rotary motion of its drive shaft (not shown) into a calibrated rotary motion of the lead screw 6 and which motion, in turn, is converted into a calibrated linear displacement of the plunger 18 via the drive nut 20.

The electrical signals that are employed for pulsing the motor 50 will be described in greater detail hereinafter, but generally the signals are applied so as to cause a fixed volume incremental dose of the medicant to be delivered to the patient. The specific incremental volume is determined by the number of openings on the encoder disc 82, the gear train ratio, the pitch of the leadscrew 6, and the bore of the syringe barrel. In the preferred embodiment, the encoder disc has 12 openings, the gear train ratio is 49 to 13, the leadscrew has 40 threads per inch, and the bore of the syringe is nominally 0.375 inches. Thus, the rotation of the pinion shaft 54, from one opening to the next of the encoder disc 82, causes one microliter of medicant to be dispensed.

Referring to FIG. 3a, a side view can be seen of the drive assembly and, in particular, the optical encoder disc 82 relative to a photo coupled encoder module 84. Specifically, it is to be noted that the optical encoder disc 82 revolves within a recess formed between two portions of the photo coupler module 84 that respectively contain a light emitting diode (LED) 86 and a photo detecting transistor 88. The detection of light from the LED 86, via the photo transistor 88, as the pinion shaft 54 rotates and exposes the openings of the encoder disc 82, thus causes a pulse to be produced, via the electronic circuitry, as each opening is exposed, but which will be described in detail hereinafter. Each pulse is then counted, via a digital counter, and again which will be described in detail hereinafter.

Referring next to FIG. 3b, a more detailed view of the optical encoder disc 82 is shown. From FIG. 3b, it is to be noted that a plurality of openings 90 (i.e. 12) have been formed through the optical encoder disc 82 at uniform spacings from one another. The openings 84, thus permit light to pass from the LED 86 to the photo transistor 88 as the pinion shaft 54 rotates. Therefore, as the motor 50 causes the pinion shaft 54 to rotate, each time an opening 84 is exposed to the photo coupler module 84, a pulse is produced, counted and stored within the control circuitry.

It is also to be recognized that while a particular optical encoder disc 82 and photo coupler module 84 have been shown with respect to the present embodiment, numerous other embodiments are possible, depending upon the peculiarities of the packaging arrangement. The primary concern of any assembly, however, is to create an assembly that is capable of producing electrical pulses via an efficient electro-mechanical arrangement. For instance, an alternative embodiment may comprise a pinion shaft 54 having permanent magnets affixed thereto so as to cause pulses to be produced as each magnet is coincident to a pickup coil.

Also, shown within the optical encoder disc 82 is an arrow 92 that indicates not only the direction of rotation of the pinion shaft 54, but also the leading edge of the openings 54 that are detected first and which must therefore be geometrically accurate. The center opening 94 of the encoder disc 82 is also formed so as to be compatibly mounted upon the pinion shaft 54 and attached thereto via a cyanoacrylic adhesive, thereby ensuring that the optical encoder disc 82 does not rotate independently by the pinion shaft 54. Again, however, the peculiar details of attachment are not critical and may be achievable through any number of well known mechanical arrangements.

Figure 4:
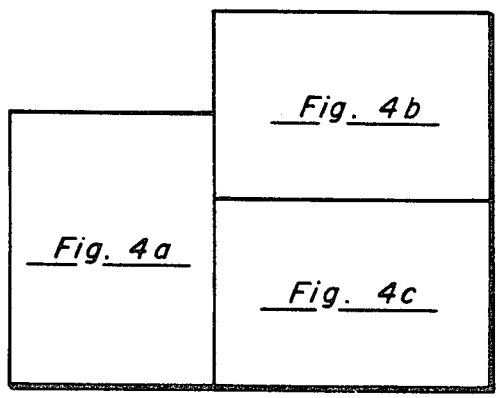
FIG. 4, comprised of Figures of 4a, 4b and 4c, shows a schematic diagram of the control circuitry that is employed in programming and controlling the various modes of operation of the present invention.
Figure 4A:
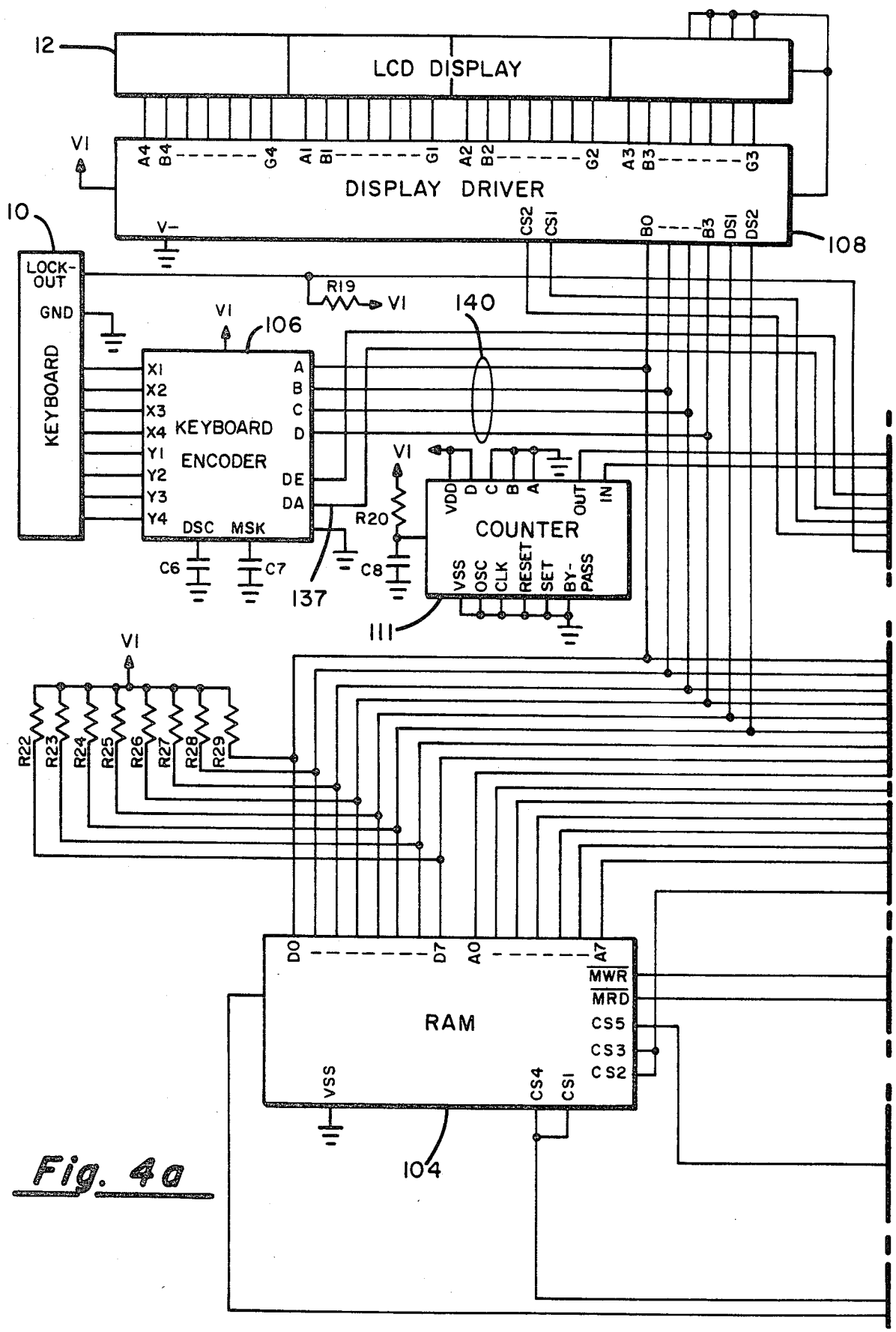
Figure 4B:
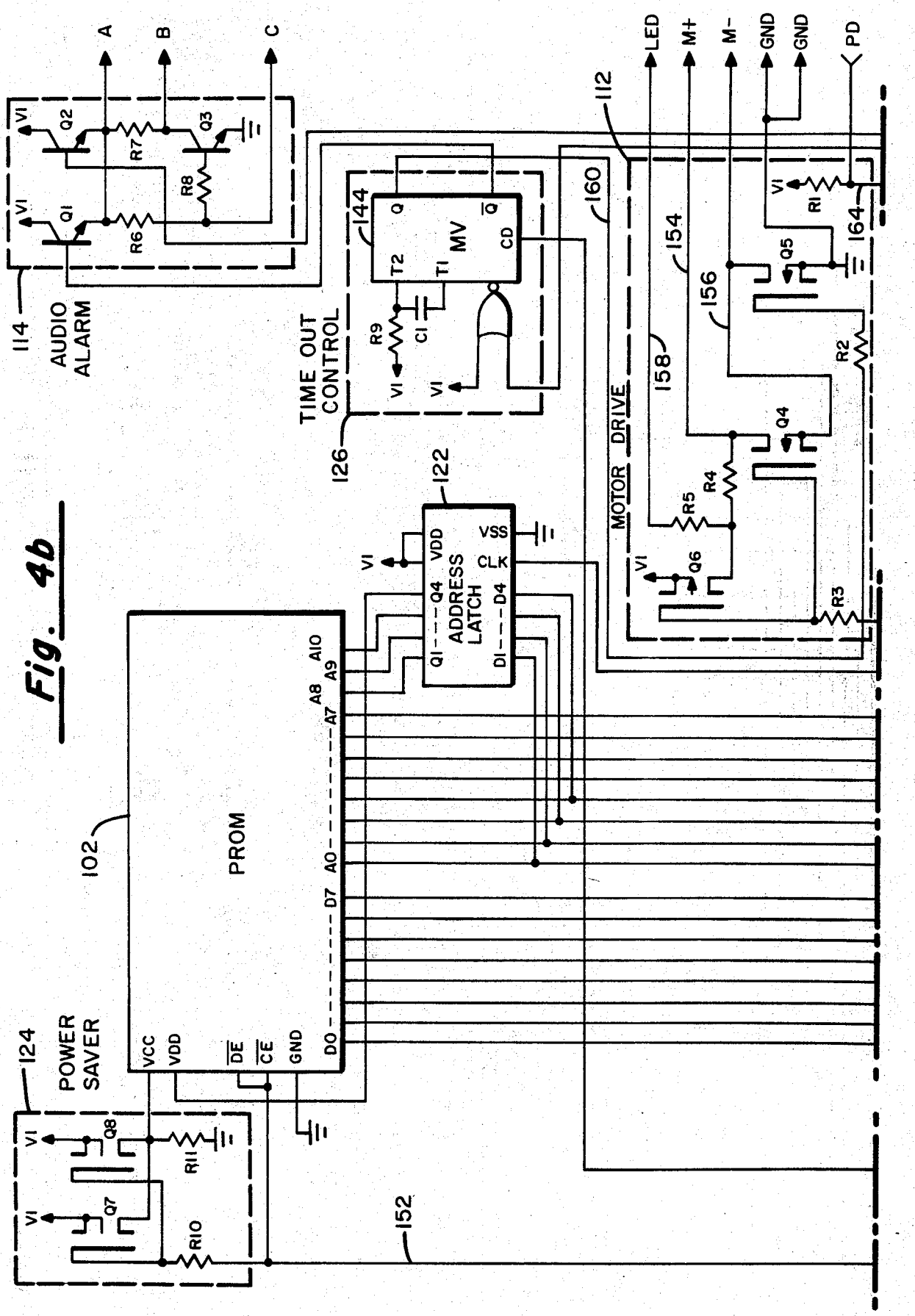
Figure 4C:
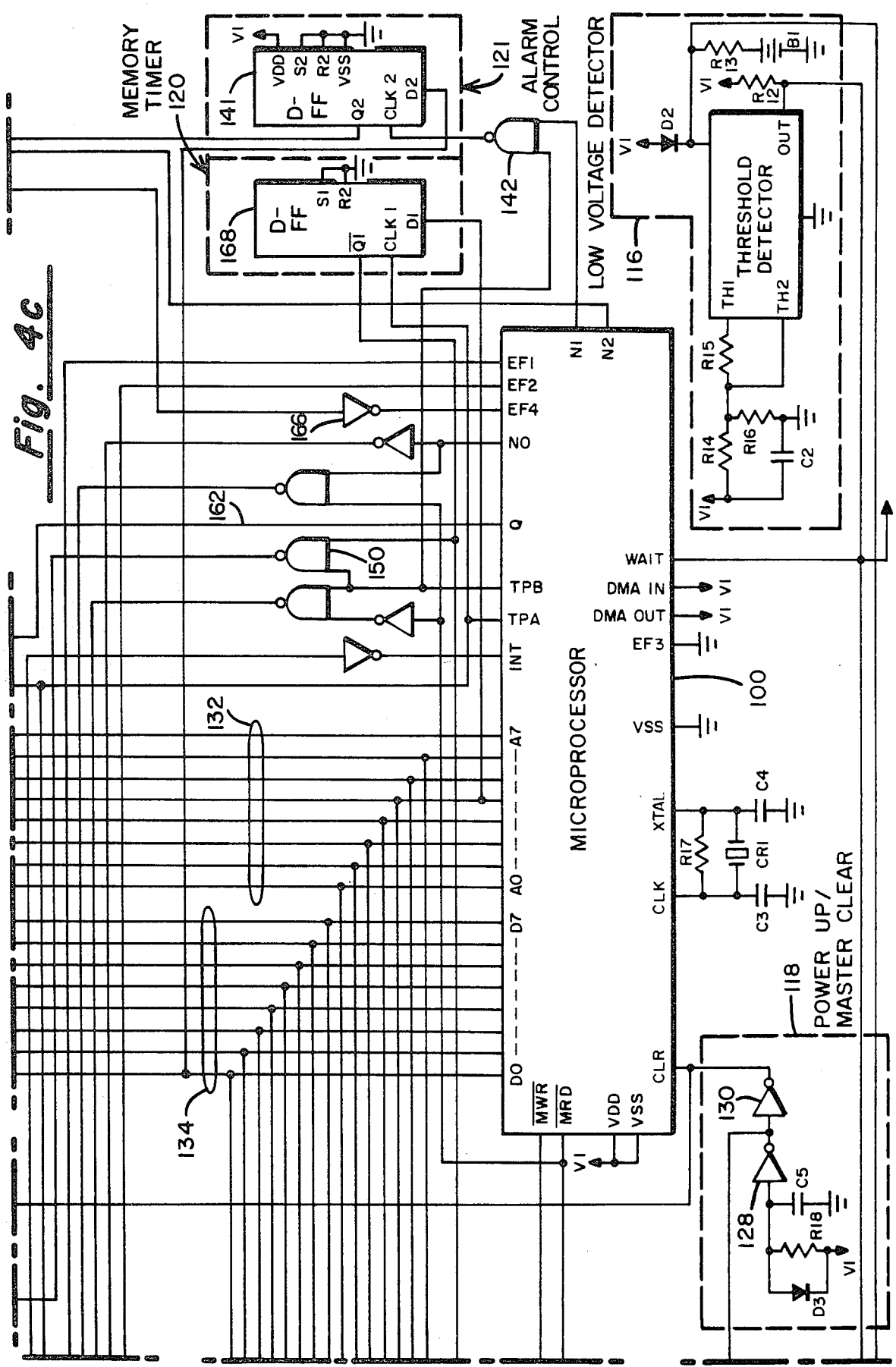

Referring next to FIG. 4, comprised of FIGS. 4a, 4b and 4c, a detailed schematic diagram is shown of the control circuitry that is used to ensure the proper operation of the present invention. As previously mentioned, the control circuitry is programmable via the use of a microprocessor 100, an associated programmable read only memory (PROM) 102 and an associated random access memory (RAM) 104. The control circuitry is also comprised of the keyboard 10, keyboard encoder 106, display driver 108, LCD display 12, motor drive 112, audio alarm 114, one second timer 111 and low voltage detector 116. Also included are the additional power up/master clear circuitry 118, memory timer 120, address latch 122, power saver 124, time out control 126 and associated peripheral logic circuitry.

Figure 5A:
FIG. 5, comprised of FIGS. 5a and 5.1 through 5.66, shows the flow diagram of the micro-program that controls the operation of the present apparatus.
Figure 5A:
Figure 5A:
Figure 5A:
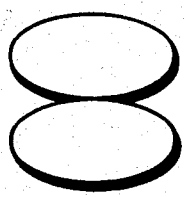
Figure 5A:

Prior to describing the operation of the control circuitry of FIG. 4, attention is directed to the flow chart of FIG. 5, comprised of FIGS. 5a and 5.1 through 5.66. The flow chart of FIG. 5 generally shows the manner of operation of the circuitry of FIG. 4, during its various modes of operation, and which will be appropriately referenced as the circuitry is described. It is to be noted, too, that the flow chart has essentially been segmented, via the various sub-figures 5.1 through 5.66, for ease of understanding. This understanding is also facilitated via FIG. 5a, wherein a key to the flow chart symbols is shown, and Table 1, below, wherein a list of the various flow chart mnemonic labels is shown relative to the figure number for the various routines and subroutines of the flow chart.

TABLE 1

INDEX TO FLOW CHART OF FIG. 5

| LABEL | FIG. | LABEL | FIG. |
|---|---|---|---|
| AG | 5.41 | MSI | 5.51 |
| Anate | 5.31 | MULT | 5.65 |
| Back | 5.37 | Pause | 5.63 |
| Back 1 | 5.15 | PCLR | 5.15 |
| Back 2 | 5.22 | Prime | 5.41 |
| Back 3 | 5.40 | PUMM | 5.43 |
| Back 4 | 5.40 | PUMP | 5.47 |
| Bascon | 5.25 | SAVP | 5.8 |
| BASDF | 5.61 | SAVP 1 | 5.2 |
| BIPP | 5.57 | SET φ | 5.64 |
| Calbi | 5.23 | SOSMI | 5.58 |
| Calbi 1 | 5.22 | SRT 1 | 5.4 |
| Check | 5.28 | SRT 2 | 5.2 |
| CK WTH | 5.3 | MLD Z | 5.22 |
| Clear | 5.15 | MLDZ 1 | 5.26 |
| CLM DUL | 5.27 | MSDR | 5.34 |
| CMSDF | 5.54 | MSDS | 5.32 |
| CONBAS | 5.19 | MSDY | 5.36 |
| DECHEX | 5.66 | MSYDS | 5.35 |
| DIV | 5.66 | SRT 13 | 5.63 |
| DK1 | 5.47 | SRT 19 | 5.40 |
| DK2 | 5.48 | SRT 21 | 5.6 |
| DK3 | 5.48 | SRT 22 | 5.4 |
| DOAL 1 | 5.21 | SRT 32 | 5.5 |
| ETER | 5.17 | STAA | 5.9 |
| ETER 1 | 5.64 | STAA 13 | 5.32 |
| FAUL 1 | 5.47 | STAA 42 | 5.10 |
| Fault | 5.38 | STEP | 5.14 |
| Fault 1 | 5.38 | STM | 5.30 |
| FLASH | 5.62 | TDS 1 | 5.48 |
| GOUT | 5.62 | TDS 2 | 5.50 |
| HEXDEX | 5.66 | Time | 5.53 |
| IEC | 5.40 | ULCT | 5.54 |
| Keyloc | 5.6 | UNITD | 5.54 |
| LOAD | 5.65 | UNSFIG | 5.61 |
| MBTN | 5.16 | UNSTFG | 5.61 |

Returning to FIG. 4, it is to be noted that the program corresponding to the flow chart of FIG. 5 is stored in the PROM 102, which typically comprises an electrically alterable PROM of a type manufactured by Intel Corporation, Model No. 2716. In order to access this program and operate the present apparatus, however, it is necessary to first initiate the power up/master clear circuitry 118 and which occurs each time a new battery pack is inserted.

At the time of insertion of a new battery pack, the microprocessor 100 is cleared and made ready for the receipt of data from the keyboard 10. A clear function is performed via the charging of capacitor C5, via resistors R18 and diode D3, so as to cause the logic inverters 128 and 130 to produce a logic "low" output until capacitor C5 charges. The logic "high" from inverter 128 is then impressed on the chip select input (CS5) of RAM 104 so as to disable the RAM 104 during the power-up period. The inverter 130 also produces a logic "low" that is impressed on the clear (CLR) input to the microprocessor 100 and which causes the microprocessor to clear its internal registers and start at address zero.

Thus, the microprocessor 100 produces a zero address value on the 8 bit address bus 132 and which address value is transmitted to the PROM 102 so as to cause the data stored therein to be read and transmitted to the microprocessor 100, via the 8 bit data bus 134. These 8 bits then cause the microprocessor 100 to pause and begin "down loading" the "SAVP" subroutine, see FIGS. 5.8 and 5.63, into the RAM 104. After down loading the SAVP subroutine, the microprocessor 100 then begins to continuously monitor the keyboard 10 to detect "whether" and "for how long" a key 8 is depressed and "which" specific key is depressed. The down loading thus permits the circuitry to not have to initiate the PROM 102 during each keyboard scan or pause loop, until after a key 8 is pressed, and then only to perform the action required, thereby saving power.

The programming of the desired functional mode and the entry of the desired parameters is thus achieved via the depression of the necessary keys 8 on the keyboard 11. The functional mode selection is achieved via the S(STEP) key and the "STEP" subroutine, see FIG. 5.14. The operator, in order to select the proper function, repeatedly depresses the key until the desired functional code appears to the left of the slash on the LCD display 12. With each depression of the STEP key the numerical value of the function code is incremented by one and therefore the operator must strike the STEP key the appropriately desired number of times so as to produce the desired function code. Attention is directed to Table 2, below, wherein the various numerical function codes of the present invention are shown with respect to the delivery of insulin. It is to be recognized though that the present invention is adaptable to other medicants requiring the same or similar functions and dose amounts.

TABLE 2

| Function Code | CODE AND A RANGE Function | Range |
|---|---|---|
| 0 | PRIME, HOLD | — |
| 1 | CONCENTRATION | 5-500 units |
| 2 | BASAL RATE | 1-100 units |
| 3 | MANUAL DOSE | 0-20 units |
| 4 | SUPPLEMENTAL DOSE | 0-50 units |
| 5 | SUPPLEMENTAL DURATION | 0-999 minutes |
| 6 | SUPPLEMENTAL DELAY | 0-999 minutes |
| 7 | ACCUMULATED DOSE | 0-999 units |
| BLANK | Pump has exited from "HOLD" mode, or "PRIME" has been cleared | |

Upon selecting the proper function code, the operator then selects the proper numerical parameter within the various ranges provided, depending upon the selected function. Thus, if the operator is programming the CONCENTRATION, the operator may select any individual concentration of between 5 and 500 units. Similarly, the operator may select a BASAL RATE (i.e. the amount of insulin delivered in a 24 hr. period, exclusive of manual meal and supplemental doses) of between 1 and 100 units. The entry of the parameter value is achieved by depressing the desired numerical keys. It is to be noted, however, that entry of the parameter values is achieved via the depression of the numerical key for the least significant numerical position first and then successively for each of the greater value numerical positions. In other words, parameter selection proceeds from right to left; and for example, for a parameter value of 99, the operator would enter a 099. Failure to enter the 0 would also be acceptable, since the microprocessor 100 would assume this, unless otherwise indicated.

Upon entering the desired function code and parameter value, the operator then depresses the E (ENTER) key so as to cause the microprocessor 100 to act upon the entered data.

It is to be recognized that as each key is depressed an 8 bit binary code is produced that is representative of the X-Y coordinates of the depressed key (i.e. 4 bits for the X coordinate and 4 bits for the Y coordinate) relative to the keyboard 10. Each 8 bit Cartesian coordinate code is then encoded via the keyboard encoder 106 so as to produce a four bit binary code and a data available (DA) signal that is transmitted via conductor 137 to the microprocessor 100. The microprocessor 100 then, when it is ready, produces a data enable (DE) signal on conductor 140 so as to cause the keyboard encoder 106 to transmit the encoded data via the four bit bus 140 to the four least significant bit positions (D0 to D3) of the 8 bit data bus 134 and the microprocessor 100. As each encoded value is received by the microprocessor 100, it is then stored within its internal registers until either an ENTER or CLEAR code has been received. It is to be noted that the depression of the STEP key does not cause the microprocessor 100 to operate on the stored data, this occurs only with the depression of any one of the ENTER, HOLD, MANUAL, CLEAR LOCKOUT or PRIME keys.

It is also to be noted that as each parameter is received by the microprocessor 100, it is decoded into its corresponding binary coded decimal (BCD) value. The microprocessor 100 then determines which digit position the data corresponds to on the LCD display 12. The BCD data for each digit is then written by the microprocessor 100 onto the data bus 134, along with the appropriate chip select (CS) and data select (DS) signals, and transmitted to the display driver 108 so as to cause the decimal value of the BCD data to be displayed on the LCD display 12 at the proper digit position. Thus, the LCD display 12 permits the operator to visibly inspect the data that is entered, via the keyboard 10, and received by the microprocessor 100, prior to its being stored in the RAM 104.

Upon reference to Table 2 and the function code of zero, it is also to be noted that a function code of zero produces either a PRIME or HOLD function, see FIGS. 5.41 and 5.63. The specific function performed depends only upon which of the H(HOLD) or P(PRIME) keys the operator depresses after the zero function code has been selected.

Further, it is to be noted that the microprocessor 100 is able to independently display messages over and above the data which is entered via the keyboard 10. In particular and for example, a message will be displayed when the PRIME function is selected. Thus, upon selecting a function code of zero and depressing the P(PRIME) key for at least one second, reference FIGS. 5.41 through 5.43, the LCD display 12 will display O/-P-. The depression of the ENTER key then causes the microprocessor 100 to react and cause the motor 50 to begin priming the syringe 4 (i.e. moving the plunger forward until all the air has been removed from the syringe 4). It is to be noted too that during a PRIME mode, priming occurs only while the ENTER key is depressed and that the PRIME mode is cleared by pressing the C(CLEAR) key.

On the other hand, depressing the zero function code and the H (HOLD) key causes the microprocessor 100 to display a O/-H- message. Similarily too, the microprocessor 100 will cause the various other messages indicated in Table 3, below, to be displayed for the various status conditions indicated.

TABLE 3

STATUS CONDITIONS

| Display | Status |
| --- | --- |
| O/-H- | HOLD |
| O/-P- | PRIME |
| /EEE | Entry error |
| H/ELP | Syringe empty motor fault or microcomputer fault |
| 6 | Supplemental delay operating* |
| 6/100 | Supplemental dose operating* |
| 7 | Device operating* |

*Underlined digit flasing.

Likewise, the display will remain blank, reference Table 2, when the pump has exited from a HOLD or PRIME mode.

After each function is programmed, the microprocessor 100, upon detecting the function code, numerical data and ENTER code, then causes an address to be produced and whereas the microprocessor 100 reads the corresponding programmed subroutine data from the PROM 102 and writes it into the RAM 104, via the appropriate memory write (MWR) and chip select signals. Subsequently, the microprocessor 100 accesses the stored subroutine data, as needed, by generating memory read (MRD) signals, concurrently with the address signals of the memory addresses that are to be read. Thus, the microprocessor 100 is able to read and write data from and into RAM 104 as it performs the various functions of Table 2.

During the BASAL mode the present apparatus delivers incremental, one micro liter doses (i.e. basal doses) at the programmed BASAL RATE, see FIG. 5.25, after programming the CONCENTRATION, see FIG. 5.19, without requiring further operator intervention. In particular, after the CONCENTRATION is programmed in units per milliliter and the BASAL RATE is programmed in units to be delivered per 24 hours, the microprocessor 100 performs the following equation, reference FIGS. 5.23 and 5.24, while rounding to the nearest second, to determine the basal interval in seconds between the incremental doses:

$$\text{BASAL INTERVAL (seconds)} = \frac{86.4 \times \text{concentration}}{\text{BASAL RATE}}$$

Thus, during the BASAL mode, the present invention delivers one microliter of medicant during each basal interval over the subsequent 24 hour period, so that the patient can be assured of obtaining the prescribed daily number of units of medicant. It is to be noted too that since the medicant, in the case of insulin, is provided in varying concentrations (i.e. U-40, U-80 and U-100), the present apparatus permits the entry of the data directly in insulin units; thus, eliminating the need to convert units to volume, according the insulin concentration used. No calculation is therefore required by the operator, since the operator need only enter the BASAL RATE (i.e. daily prescribed number of basal insulin units) and the CONCENTRATION (i.e. most typically 40, 80 or 100).

The operator therefore need only concern himself or herself with the additional dosages that are prescribed and which may be administered via the present apparatus as a MANUAL dose (i.e. a single dose of insulin delivered immediately at a rapid rate, also known as a bolus or "burst" dose) or as a SUPPLEMENTAL dose (i.e. a dose of insulin distributed over an extended time following a desired time delay) or both. The details of the delivery of the MANUAL and SUPPLEMENTAL doses, will be described in greater detail hereinafter.

In order to illustrate the above explanation of the BASAL mode and by way of some examples, assuming that a patient requires a total daily basal dosage of 12 insulin units, then depending upon the concentration of the insulin, the following basal intervals will be calculated and the following number of basal doses will be delivered:

EXAMPLE 1

If U-100 insulin is used, then the basal interval is calculated via the microprocessor 100 to be 12 minutes. Thus, the apparatus will dispense a one microliter dose of the U-100 insulin each and every twelve minutes during the 24 hour period or a total dosage of 120 one microliter basal doses.

EXAMPLE 2

If U-40 insulin is used, the basal interval is four minutes and 48 seconds. Thus, 300 one microliter basal doses will be dispensed during the 24 hour period.

EXAMPLE 3

If U-25 insulin is used, the basal interval is 3 minutes. Thus, 480 one microliter basal doses will be delivered during the 24 hour period.

It is to be recognized that because the present apparatus is programmable in whole numbers only, greater precision may be obtained by diluting the prescribed insulin concentrations so as to produce a greater degree of precision in the supply of the medicant. Also, if fractional units of medicant are prescribed, such dilution will better enable the delivery of the fractionally prescribed amount.

Returning to the description of FIG. 4 and the programming of the various other modes and parameters, it is to be noted that upon entering a desired function and parameter, and depressing the ENTER key, the apparatus, in addition to displaying the entry, confirms the entry of the data into the RAM 104 via a short audible "beep" signal. If, however, a value outside the specified range for the programmed parameter is entered, the error message (i.e./EEE) displayed on the LCD display 12, and the audible signal continues, until a new number is entered or the CLEAR key is depressed.

The audio alarm circuit 114 of the present invention is comprised transistors Q1, Q2 and Q3 and which are coupled in a self oscillating fashion so as to produce an audible warning signal of 3 Khz. The audible warning occurs when a time pulse B(TPB) and an audio enable signal from terminal N1 of microprocessor 100 initiate the alarm control circuitry 121 and cause the clocking of the D flip flop 141, via NAND gate 142. D flip flop 141 then produces a base drive signal to transistor Q2, which, in turn, causes the alarm circuit 114 to self-oscillate and produce the audible alarm signal. Similarily, if a time out condition occurs, and which can only happen during a microcomputer fault via the absence of a signal from the N2 terminal of the microprocesor 100, the time-out control circuitry 126 times out and transmits a signal from the Q terminal of one-shot 144 that causes transistor Q1 to initiate the self-oscillation.

The time-out control circuitry 126 is comprised of the retriggerable one shot multi-vibrator 144 and its associated internal NOR gate which couples the signals from conductor 148 and the N2 terminal of the microprocessor 100 to the multi-vibrator 144. It should be noted that the occurrance of a time-out condition indicates to the operator, that the microprocessor 100 is not operating properly, since the multi-vibrator 144 should be reset at regular intervals. It should also be noted that alarm signals can occur during various other conditions and which other conditions can be found upon reference to Table 4, below, and FIGS. 5.38, 5.40 and 5.48.

TABLE 4
ALARM CONDITIONS

Illegal Entry. When a value outside the acceptable range is entered, /EEE appears in the display and a tone sounds. Entering a new value or depressing the C key clears the display and stops the tone.

Low Battery. When the battery voltage falls below an acceptable level, a tone sounds until the battery pack is removed. (FIGURES showing in the display are frozen at the time the alarm sounds.) The pump discontinues delivery in this condition, but, the data stored in memory is protected for at least 30 minutes.

Motor Fault. If the motor or any part of the drive train fails to operate for any reason, H/ELP appears in the display and a tone sounds. Depressing the C key stops the alarm and automatically places the device in the HOLD. Depressing the H key until O/-H-appears reactivates the pump.

Microcomputer Fault. If the microcomputer fails to send a message to the pump's fail-safe (i.e. time out control 126) circuitry at regular intervals to the inform it that the microcomputer is operating properly, the alarm will sound and delivery will be discontinued. The alarm for this fault is similar to the LOW BATTERY alarm, with the exception that battery replacement may not correct the fault.

Syringe Empty. If the syringe is allowed to bottom out, the pump will respond as above, with /HELP appearing in the display.

As mentioned, the present apparatus also permits the programming of a MANUAL dose and a SUPPLEMENTAL dose over and above the BASAL dose. The dose dispensed during the MANUAL mode is essentially a single burst of insulin, delivered as the user desires, see FIGS. 5.22, 5.26, 5.27 and 5.28. The dose is programmed via the entry of a function code of 3 and the desired MANUAL DOSE (i.e. 0–20 units). The microprocessor 100, upon the entry of the dosage, then accesses the previously programmed CONCENTRATION and calculates the dose to be delivered in microliters, via the following equation, while rounding to the nearest microliter:

$$\text{MANUAL DOSE (microliters)} = \frac{1{,}000 \times \text{MANUAL DOSE}}{\text{CONCENTRATION}}$$

Next, upon depressing the M key, a beep will sound and the programmed dosage will be delivered immediately as a successive number of incremental basal doses. Upon completing the delivery of the MANUAL dose, another beep will sound and the MANUAL DOSE location in the RAM 104 will be reset to 0. It is to be noted that if the device were programmed in a HOLD mode, the thus entered MANUAL dose would not be delivered.

Furthermore, if the syringe were emptied during the delivery of the MANUAL dose, the alarm would sound and H/ELP would appear on the display 12. The operator would then have to clear the alarm and replace and PRIME the syringe 4, prior to returning to the MANUAL mode, via the depression of the M key, once again. The remainder of the MANUAL dose would then be delivered upon this subsequent depression.

The SUPPLEMENTAL dose mode of operation also permits the operator to deliver a dosage over and above the incremental basal doses, after a timed delay. This mode permits diabetics to compensate for the nocturnal glucose rise that often occurs during sleep. Thus, the SUPPLEMENTAL dose is administered during mid-sleep and accordingly requires that the patient program a SUPPLEMENTAL DOSE, SUPPLEMENTAL DURATION and SUPPLEMENTAL DELAY PARAMETER. The microprocessor 100 then computes the appropriate interval between one microliter increments, again rounding to the nearest second, but will not deliver the SUPPLEMENTAL DOSE until after the delay period has expired.

The SUPPLEMENTAL mode is selected upon programming each of the above parameters. In particular, the SUPPLEMENTAL DOSE is established via the entry of a function code of 4 and the number of units (i.e. 0–50) to be delivered, see FIG. 5.32 The SUPPLEMENTAL DURATION is established via entering a function code of 5 and the number of minutes (i.e. 0–999) over which the SUPPLEMENTAL DOSE is to be delivered, see FIG. 5.34. Finally, the SUPPLEMENTAL DELAY or period of time prior to the delivery of the SUPPLEMENTAL DOSE is established, via the entry of a function code of 6 and the desired delay period, see FIG. 5.35. It is also to be noted that each of the above supplemental parameters are entered via the depression of the E key.

The entry of the SUPPLEMENTAL DOSE, SUPPLEMENTAL DURATION AND SUPPLEMENTAL DELAY data then permits the microprocessor 100 to calculate the proper SUPPLEMENTAL INTERVAL in seconds and the appropriate total SUPPLEMENTAL DOSE in microliters. These values are calculated as per the following equations, see also FIGS. 5.32 through 5.37 and FIGS. 5.51 and 5.52.

$$\text{SUPPLEMENTAL INTERVAL (seconds)} = \frac{6 \times \text{SUPP. DURATION} \times \text{CONCENTRATION}}{\text{SUPPLEMENTAL DOSE} \times 100}$$

$$\text{SUPPLEMENTAL DOSE (microliters)} = \frac{1000 \times \text{SUPPLEMENTAL DOSE}}{\text{CONCENTRATION}}$$

The activation of the SUPPLEMENTAL mode is then initiated upon again entering a function code of 6 and depressing the M key, which starts the timing out of the SUPPLEMENTAL DELAY period. Also, upon the depression of the M key, the function code (6) will begin to flash in the LCD display 12 as the one second counter 111 counts down at a 1 hertz rate until the delay period has expired, see FIGS. 5.54 through 5.56.

Upon the timing out of the delay interval, the microprocessor 100 will then cause the delivery of the calculated SUPPLEMENTAL DOSE in one microliter increments, one increment per each SUPPLEMENTAL INTERVAL, until the entire SUPPLEMENTAL DOSE has been delivered. Upon starting delivery, the function code (6) will also stop flashing and the first numerical digit of the programmed SUPPLEMENTAL DURATION will begin to flash and continue to do so until the entire SUPPLEMENTAL DOSE has been delivered, see FIGS. 5.58 through 5.60.

It is to be noted that the SUPPLEMENTAL mode may be deactivated at any time by depressing the C key. It is also to be noted that if the apparatus is in a HOLD mode, the microprocessor 100 will ignore the depression of the M key so that the SUPPLEMENTAL DELAY period will not be activated.

The present apparatus also maintains a record of the total ACCUMULATED DOSE delivered since the last reset, power up/master clear condition or changing of the battery pack B1. The total ACCUMULATED DOSE can be selectively monitored by the patient via the entry of a function code of 7. Upon this entry, the microprocessor 100 causes the total ACCUMULATED DOSE to be displayed on the LCD display 12. Upon reading the value, the patient can then reset the display by depressing the C key. Otherwise, the microprocessor 100 continue to maintain a record of the total ACCUMULATED DOSE. Also, upon changing the batteries or changing the concentration value, the microprocessor 100 will automatically reset the ACCUMULATED DOSE.

Referring again to FIG. 4, it is to be noted that a number of additional functional circuit elements have been included in the present apparatus, but which have not been discussed in any detail heretofore. In particular, it is to be noted that when the microprocessor 100 addresses PROM 102, which is comprised of two kilobytes of preprogrammed data, it does so in a multiplexed fashion over two clock cycles. During the first clock cycle, the three most significant bits of the address value are stored in the address latch 122. During the second clock cycle, the next eight bits of the address, along with the first three bits, are impressed on PROM 102 so as to select the desired data. It is also to be noted that the present apparatus for an additional address bit so that four kilobytes of data could be accomodated in PROM 102.

The "power saver" circuitry 124 is used in conjunction with PROM 102, via the CMOS transistors Q7 and Q8, and which transistors act as a switch, and permit the microprocessor 100 to power down PROM 102 when the microprocessor 100 is not accessing the PROM 102. Because each access to PROM 102 requires approximately 100 milliamps of current, it is desirable to have some sort of switch intermediate PROM 102 and the microprocessor 100. This switching function is achieved via transistors Q7 and Q8 and which conduct only when gate drive is present on conductor 152. It is also to be noted that transistors Q7 and Q8 have been coupled in parallel so that when the microprocessor 100 produces the gate drive, via NAND gate 150, the source to drain impedance of the transistor combination of Q7 and Q8 is reduced and the power loss due to the switching action is also minimized.

Turning now to the photo-coupled motor drive circuitry 112, it is to be noted that it is generally comprised of three transistors Q4, Q5 and Q6. The transistors, in turn, are coupled to the M+ and M− terminals of the motor 50, via conductors 154 and 156, and to the LED 74, via conductor 158. The motor drive circuitry 112 operates upon the receipt of a gate drive signal to transistors Q4 and Q6 via conductor 162 and the Q output terminal of the microprocessor 100. The gate drive, in turn, turns transistor Q4 "off" and transistor Q6 "on". The conduction of transistor Q6, in turn, energizes the windings of the motor 50 so as to cause the rotation of drive shaft 66 and the consequent delivery of the medicant to the patient. Transistor Q5 is normally "on" bus if the timeout control (144) times but, transistor Q5 is turned "off", thus preventing motor movement. Similarly the M+ windings and LED 74 are energized by the conduction of transistor Q6.

The microprocessor 100, in order to brake the motor and stop the delivery of medicant, subsequently produces braking signals via its Q terminal and conductor 162 and which drive the gates of transistors of Q4 and Q6, thereby turning transistor Q4 "on" and transistor Q6 "off" and which produces the dynamic braking of the motor 50. This dynamic braking occurs due to the shunting of the M+ and M− terminals of motor 50. It is to be noted though that the resistor R4, provides a torque limiting effect so as to produce a smooth reduction in the motor speed. The resistors R2 and R3, in turn, act to reduce any parasitic oscillations in the signals on conductors 160, 162.

It is to be noted too that as the output shaft 54 of the motor 50 turns, the LED 74 is energized, so that light pulses are generated via the passing of the optical encoder disc 82 through the infra-red beam of light produced by the LED 86. The light pulses are then converted into electrical pulses, upon detection by the photo detecting transistor 88. The pulses generated by the photo transistor 88 are then received at the PD terminal and transmitted via conductor 164 to inverter 166 and the EF 4 terminal of the microprocessor 100. The microprocessor 100 then causes the pulses, to be counted, see FIG. 5.47, until the preprogrammed number of pulses have been counted, when it next causes the dynamic braking and which count is indicative of the delivery of one microliter of medicant. The duration of the motor drive may thus vary from basal interval to basal interval, since the volume of the dose is directly related to the rotation of the motor drive shaft 66 and not the characteristics of the motor drive signals.

Next, referring to the memory timer 120, it is to be noted that it is essentially comprised of D flip flop 168. In particular, flip flop 168 operates in a strobed fashion to control the gate drive to the power saver circuitry 124 by monitoring the A4 address terminal of the microprocessor 100. Recalling that the PROM 102 is addressed in in a multiplexed fashion, a signal is present of the A4 terminal only during the second half of the clock cycle, when it is necessary to ensure that the PROM 102 is powered up. Thus, by clocking flip flop 168 at this time, the necessary gate drive is provided to the power saver circuitry 124, at the same time as the TPB signal via NAND gate 150 and conductor 152, so that PROM 102 will be powered up. At the same time, the Q1 signal ensures that RAM 104 is deselected by coupling the signal to the CS3 and CS2 terminals thereof.

D flip flop 140 of the alarm control circuitry 121, on the other hand, acts in response to the signals from the microprocessor 100 to NAND gate 142 and the presence of data on the D0 terminal of the microprocessor 100 so as to control the gate drive to the audio alarm circuitry 114.

The low voltage protection circuitry 116 is also coupled between the microprocessor 100 and the main battery pack and acts to, at all times, monitor the battery voltage. In particular, the low voltage detector 116 monitors the battery voltage as the circuitry "powers up", as well as when it "powers down". Generally, it acts to produce a threshold voltage, via resistors R14, R15 and R16 and capacitor C2, that must be exceeded before the circuitry of FIG. 4 will become active. It is to be noted though that the voltage threshold will vary depending upon whether the voltage is rising or falling and which thus reflects a hysteresis effect. In general though, so long as the voltage from the battery pack B1 exceeds the threshold voltage, a logic signal is produced on the output port of the low voltage detector 116 that enables the chip select ports CS4 and CS1 of the RAM 104. If, however, the voltage of the voltage source B1 falls below the threshold voltage, a logic signal will be produced that will disable the RAM 104, as well as force the microprocessor 100 in a "wait" condition, until the supply voltage level has again exceeded the threshold voltage.

Also, while not previously described and while not shown in detail, it is to be noted that, the present apparatus is battery powered via a rechargable battery pack (not shown) that is contained within container 10, below the keyboard 10. A battery compartment cover (not shown) is provided on the right side of the container 2 and is slidably mounted thereon and affixed thereto via a latch arrangement similar to that for the latch 28. The battery pack is designed to provide approximately 24 hours of operation, but should the battery pack fail, the emergency battery pack B1, which charges from the main battery pack, will protect the contents of RAM 104 for approximately 30 minutes. Should the charge on the main battery pack become too low, the microprocessor 100 will enter the "wait" mode, sound an alarm, freeze the characters on the LCD display 12 and stop the pump operation, until a new battery pack is inserted.

Upon inserting a new battery pack, the operator should then check the programmed parameters to determine whether data has been lost. Such a check is accomplished by successively depressing the select key so as to cause the microprocessor 100 to read the data from the RAM 104 for each function code as it is called up on the display 12. If any errors are detected, the operator need then only reprogram those individual functions. If, however, the low battery condition persisted for over 30 minutes, it is most likely that all the data will have been lost and the operator will have to reprogram all the functions.

The present apparatus also permits the operator to select a LOCK-OUT function, whereby the operator, upon depressing the L key for at least four seconds, causes the microprocessor 100 to enter the LOCK-OUT function and thereafter prevent any inadvertant re-programming from occuring. Upon the depression of the L key, a beep sounds, and upon the timing out of the four seconds a second beep sounds, confirming the entering of the LOCK-OUT mode, see FIGS. 5.6, 5.7 and 5.8. The apparatus may, however, be reactivated, by merely repeating the above operation. It is also advantagous for the operator, just prior to programming the LOCK-OUT function, to call up the function code 7 (i.e. ACCUMULATED DOSE) so that upon entering the LOCK-OUT function, the ACCUMULATED DOSE will thereafter be continuously displayed on the LCD display 12.

While the present invention has been described with particular reference to its preferred embodiment, as an insulin pump, variations thereon may suggest themselves to those of skill in the art upon a reading hereof. The following claims should therefore be interpreted as so to encompass equivalent structures within the spirit of the claimed invention.

What is claimed is:

1. A portable programmable infusion pump comprising in combination:
   means for containing a medicant;
   means for evacuating said containment means;
   keyboard means for programming a medicant concentration, at least one medicant delivery mode of operation and dosage data for each programmed mode, said dosage data including a total dose to be delivered over a predetermined length of time for each programmed mode;
   memory means for storing a microprogram, each programmed mode, said medicant concentration and said dosage data;
   processing means responsively coupled to said memory means for determining the volume of an incremental dose and for controlling the rate at which said evacuation means delivers one or more of said incremental doses during each programmed delivery mode.

2. A portable programmable infusion pump as set forth in claim 1 wherein during a first programmed delivery mode said processing means in response to the programmed medicant concentration and the dosage data for said first delivery mode determines a first interval and controllably causes the delivery of one of said incremental doses of medicant once each of said first intervals over a predetermined first length of time.

3. A portable programmable infusion pump as set forth in claim 2 including a second programmed delivery mode and during which said processing means in response to the programmed medicant concentration and the dosage data for said second delivery mode, consecutively and continuously controls the delivery of a determined number of said incremental doses of medicant.

4. A portable programmable infusion pump as set forth in claim 3 including means for delaying the onset of the delivery of the incremental doses for said second delivery mode until a delay period of a predetermined length of time has elapsed.

5. A portable programmable infusion pump as set forth in claim 2 including a third programmed delivery mode and during which said processing means in response to the programmed medicant concentration and the dosage data for said third delivery mode determines a third interval and controllably causes the delivery of one of said incremental doses of medicant once each of said third intervals over a predetermined third length of time.

6. A portable programmable infusion pump as set forth in claim 5 wherein said processing means for one or the other of said programmed first and third modes, independent of the other programmed mode, causes the delivery of one of said incremental doses during one or more of the other mode's first or third intervals.

7. A portable programmable infusion pump as set forth in claim 1 including means maintaining a selectively accessible record of the accumulated number of incremental doses delivered by said evacuation means for permitting a determination of the total dosage of medicant delivered relative to a known delivery start time.

8. A portable programmable infusion pump as set forth in claim 1 including means for selectively programming a lock out condition and thereby preventing the further programming or reprogramming of said infusion pump during said lock out condition.

9. A portable programmable infusion pump as set forth in claim 1 wherein said evacuation means includes a refillable syringe and means for controllably evacuating any air within said syringe in response to a programmed prime fuction.

10. A portable programmable infusion pump as set forth in claim 1 including selectively actuable display means for visibly confirming the entry of each delivery mode, said medicant concentration and said dose data into said memory means and for displaying error messages or predetermined status conditions during the operation of said infusion pump.

11. A portable programmable infusion pump as set forth in claim 1 including photo coupled detector means for monitoring the mechanical movement of said evacuation means during the delivery of each of said incremental doses and wherein said processing means compares said detected movement to said determined incremental volume to ensure the delivery of a constant volume of medicant with each incremental dose.

12. A portable programmable infusion pump as set forth in claim 11 including a syringe and axially operable plunger, a driven lead screw coupled to said plunger for axially moving said plunger with the rotational movement of said lead screw and a multi-apertured member mounted relative to said lead screw and wherein said photo coupled detector means monitors the mechanical movement of said lead screw relative to said apertures, the space between each aperture corresponding to the delivery of a predetermined volume of medicant.

13. A portable programmable infusion pump as set forth in claim 1 including emergency power supply means separate from a primary power supply and responsive to a low primary power supply condition for maintaining power to said infusion pump for a finite period, and during which period said infusion pump suspends the delivery of medicant and produces an alarm condition.

14. A portable programmable infusion pump as set forth in claim 1 wherein each incremental dose is one microliter and said medicant concentration is programmed in standard units of medicant per millimeter.

15. A portable programmable infusion pump comprising:
means for containing a medicant;
means for evacuating said containment means;
keyboard means for programming a plurality of medicant delivery modes of operation, one of a plurality of medicant concentrations and dosage data for each programmed delivery mode, said dosage data including a total dose to be delivered over a predetermined length of time;
memory means for storing an operating microprogram, said programmed medicant concentration, said programmed medicant delivery modes and said dosage data; and
processing means responsively coupled to said memory means for determining the volume of an incremental dose and a delivery rate for each programmed mode and for correspondingly controlling the rate at which said evacuation means delivers one or more of said incremental doses during each of said programmed modes.

16. A portable programmable infusion pump as set forth in claim 15 wherein said processor, depending upon the dosage data for each of said programmed modes and the programmed medicant concentration, determines an incremental dose-to-dose interval for each programmed delivery mode and causes said evacuation means to deliver an incremental dose of said medicant once each determined dose-to-dose interval during each mode until each mode's programmed total dose is delivered.

17. A portable programmable infusion pump as set forth in claim 16 wherein each delivered incremental dose is one microliter.

18. Apparatus as set forth in claim 15 wherein said processing means for each of said programmed modes, independent of the other programmed mode or modes, causes the delivery of one of said incremental doses during each of a determined dose-to-dose interval for one or more modes.

19. A portable programmable infusion pump comprising:
a tubular syringe mounted in a patient transportable container for containing a medicant and having a plunger axially coupled thereto;
driven lead screw means mounted in coaxial relation to said plunger for axially moving said plunger to and fro;
keyboard means for programming a plurality of medicant delivery modes of operation, one of a plurality of medicant concentrations and dosage data for each programmed delivery mode, said dosage data including a total dose to be delivered over a predetermined length of time;
memory means for storing an operating microprogram, said medicant concentration, said programmed delivery modes and said dosage data; and
processing means responsively coupled to said memory means for determining an incremental dose-to-dose delivery interval for each programmed delivery mode and for correspondingly controlling said driven lead screw means so as to deliver a predetermined volume of said medicant during each dose-to-dose interval for each of said programmed modes, thereby delivering a desired dosage profile to said patient over time.

20. An improved patient transportable, programmable infusion pump having a medicant storage chamber and means for controllably evacuating the storage chamber and delivering the medicant to a patient in response to one or more programmed medicant delivery modes, the improvement comprising:
means for programming at least one of a plurality of medicant concentrations that may be dispensed by said infusion pump; and
means responsive to said programmed medicant concentration and each of said programmed delivery modes for determining the volume of an incremental dose and a dose-to-dose interval between the delivery of each incremental dose for each of said delivery modes, and whereby said infusion pump delivers said medicant in a predetermined delivery profile over time.

21. An improved infusion pump as set forth in claim 20 wherein the volume of the determined incremental dose for each mode is predetermined to be a constant and the same for each mode and whereby said infusion pump delivers said medicant in a predetermined delivery profile over time.

22. In an infusion pump having medicant containing means and means for producing volume controlled incremental doses of medicant, the improvement comprising:

means responsive to a plurality of initially programmed medicant delivery modes for determining a rate of delivery over time for each mode, independent of the other modes, for a plurality of incremental doses and for delivering the incremental doses of said medicant at each mode's determined rate, whereby over time the incremental doses are delivered as a desired delivery profile.

* * * * *

UNITED STATES PATENT AND TRADEMARK OFFICE
CERTIFICATE OF CORRECTION

PATENT NO. : 4,529,401

DATED : July 16, 1985

INVENTOR(S) : James E. Leslie et al

It is certified that error appears in the above-identified patent and that said Letters Patent are hereby corrected as shown below:

Column 17, Line 50, "millimeter" should read -- milliliter --.

Signed and Sealed this

Fifteenth Day of October 1985

[SEAL]

Attest:

Attesting Officer

DONALD J. QUIGG

Commissioner of Patents and Trademarks—Designate